United States Patent [19]
Carroll

[11] 3,994,939

[45] Nov. 30, 1976

[54] PROCESS FOR PRODUCTION OF 6-AMINO-2,2-DIMETHYL-3-(5-TETRAZOLYL)PENAM AND CERTAIN DERIVATIVES THEREOF

[75] Inventor: Ronnie D. Carroll, East Lyme, Conn.

[73] Assignee: Pfizer Inc., New York, N.Y.

[22] Filed: Oct. 29, 1974

[21] Appl. No.: 518,275

Related U.S. Application Data

[63] Continuation-in-part of Ser. No. 450,436, March 12, 1974, abandoned.

[52] U.S. Cl. .......................... 260/306.7 R; 424/271
[51] Int. Cl.$^2$ ......................................... C07D 277/00
[58] Field of Search ................ 260/308 D, 306.7 C, 260/306.7 R

[56] References Cited
UNITED STATES PATENTS

| | | | |
|---|---|---|---|
| 3,427,302 | 2/1969 | Essery | 260/308 D |
| 3,663,563 | 5/1972 | Fosker et al. | 260/306.7 C |
| 3,860,585 | 1/1975 | Carroll et al. | 260/306.7 C |

*Primary Examiner*—Raymond V. Rush
*Attorney, Agent, or Firm*—Connolly and Hutz

[57] ABSTRACT

A chemical process which comprises reacting 6-(2-phenylacetamido)- or 6-(2-phenoxyacetamido)-2,2-dimethyl-3-(5-tetrazolyl)penams and certain derivatives thereof which carry a blocking or pseudo blocking group on the tetrazolyl moiety with a halogenating agent at or below 0° C. to form the corresponding imino halide, followed by reaction of the imino halide with an alcohol below about −20° C. to form the corresponding imino ether, and hydrolyzing the imino ether under acid conditions. The preparation of the starting 6-acyl-2,2-dimethyl-3-(5-tetrazolyl)penams is described.

5 Claims, No Drawings

PROCESS FOR PRODUCTION OF 6-AMINO-2,2-DIMETHYL-3-(5-TETRAZOLYL)PENAM AND CERTAIN DERIVATIVES THEREOF

CROSS-REFERENCE TO RELATED APPLICATIONS

This application is a continuation-in-part of copending application Ser. No. 450,436, filed Mar. 12, 1974 and now abandoned.

BACKGROUND OF THE INVENTION

1. Field of the Invention

This invention relates to a process for the production of 6-amino-2,2-dimethyl-3-(5-tetrazolyl)penams. More particularly, it relates to a chemical process for the conversion of 6-acylamido-2,2-dimethyl-3-(5-tetrazolyl)penams, and especially of 6-(2-phenylacetamido)- and 6-(2-phenoxyacetamido)-2,2-dimethyl-3-(5-tetrazolyl)penams and certain derivatives thereof which carry a blocking or pseudo blocking group on the tetrazolyl moiety, to 6-amino-2,2-dimethyl-3-(5-tetrazolyl)penams.

2. Description of the Prior Art 6-amino-2,2-dimethyl-3-(5-tetrazolyl)penam (formula I below and certain derivatives thereof wherein a blocking or pseudo blocking group is attached to the 1- or 2- position of the tetrazolyl moiety are valuable intermediates for the sythesis of a new class of antibacterial agents; namely, 6-acylamido-2,2-dimethyl-3-(5-tetrazolyl)penams. Such compounds are described in U.S. application Ser. Nos. 407,097, 450,435, and 491,510 filed Oct. 17, 1973, Mar. 12, 1974 and July 24, 1974 respectively, each of said applications now being abaondoned.

The chemical cleavage of acyl side chains from penicillins and cephalosporins is described in U.S. Pat. No. 3,499,909. The process comprises protection of the carboxyl groups of the penicillins or cephalosporins by converting them to silyl esters. The silyl esters are then reacted with a halogenating agent below about 0° C. to produce an imino chloride which is then treated with an alcohol below about −20° C. The imino ether thus produced is then hydrolyzed under acid conditions to provide 6-aminopenicillanic acid or 7-aminocephalosporanic acid.

For the sake of convenience, the compounds described herein are identified as derivatives of penam. The term "penam" has been defined by Sheehan et al. in the Journal of the American Chemical Society, 75 3293 (1953), as referring to the structure

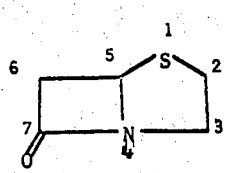

Using this terminology, the well-known antibiotic penicillin G is designated as 6-(2-phenylacetamido)-2,2-dimethyl-penam-3-carboxylic acid.

Many of the reactants of this invention are also 5-substituted tetrazoles, and 5-substituted tetrazoles can exist in two isomeric forms, viz:

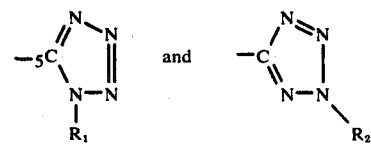

As will be appreciated by one skilled in the art, when the substituent represented by $R_1$ or $R_2$ is hydrogen, the two forms co-exist in a dynamic tautomeric, equilibrium mixture. However, in the case where $R_1$ or $R_2$ represent a substituent other than hydrogen, the two forms represent different chemical entities which do not spontaneously interconvert.

SUMMARY OF THE INVENTION

The process of this invention for producing a 6-amino-2,2-dimethyl-3-(5-tetrazolyl)penam compound of the formula

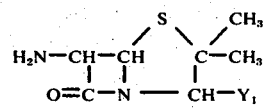

wherein $Y_1$ is selected from the group consisting of

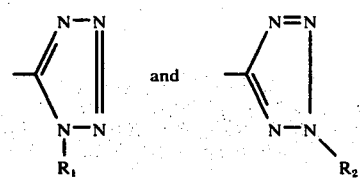

wherein $R_1$ is selected from the group consisting of $R_2$ and a tetrazolylpenam nitrogen protecting group, the nature of which is defined below;

$R_2$ is selected from the group consisting of hydrogen, trialkylsilyl having from one to four carbon atoms per alkyl group, alkanoyloxymethyl having from three to eight carbon atoms, 1-alkanoyloxyethyl having from four to nine carbon atoms, phthalidyl and

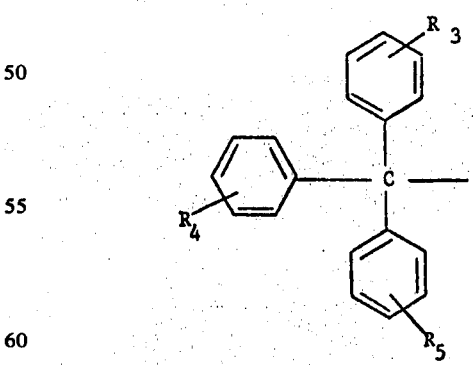

wherein $R_3$, $R_4$, and $R_5$ are each selected from the group consisting of hydrogen, chloro, bromo, fluoro, alkyl having from one to four carbon atoms, alkoxy having from one to four carbon atoms and phenyl. comprises: a. reacting a compound selected from the group consisting of

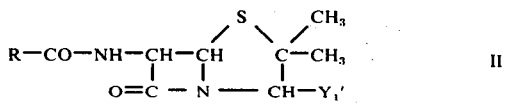

wherein R is selected from the group consisting of benzyl and phenoxymethyl; and wherein $Y_1'$ is selected from the group consisting of

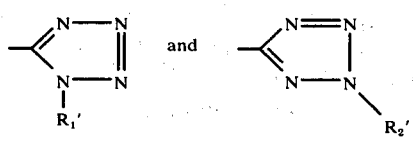

wherein $R_1'$ is selected from the group consisting of $R_2'$ and a tetrazolylpenam nitrogen protecting group;

$R_2'$ is selected from the group consisting of trialkylsilyl having from one to four carbon atoms per alkyl group, alkanoyloxymethyl having from three to eight carbon atoms, 1 alkanoyloxyethyl having from four to nine carbon atoms, phthalidyl and

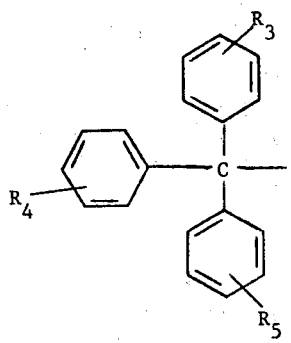

wherein $R_3$, $R_4$, and $R_5$ are each selected from the group consisting of hydrogen, chloro, bromo, fluoro, alkyl having from one to four carbon atoms, alkoxy having from one to four carbon atoms and phenyl, under anhydrous conditions with a halogenating agent at a temperature below about 0° C. to form the corresponding imino halide;

b. reacting the said imino halide at a temperature below about —20° C. with an alcohol of the formula R'—OH wherein R' is selected from the group consisting of alkyl of 1 to 12 carbon atoms, phenylalkyl of 1 to 7 alkyl carbon atoms, hydroxyalkyl of 2 to 12 carbon atoms, alkoxyalkyl of 3 to 13 carbon atoms, monocyclic aryloxyalkyl of 2 to 7 alkyl carbon atoms, monocyclic aralkoxyalkyl of 4 to 7 alkyl carbon atoms, and hydroxy-alkoxyalkyl of 4 to 7 carbon atoms to form the corresponding imino ether, and c. reacting the said imino ether under aqueous acid conditions to cleave the imino double bond.

The process is broadly applicable to a wide variety of compounds of formula II wherein R represents an organic acyl group which does not react with the halogenating agent. The choice of such compound is largely determined by factors of availability and economics. For such reasons, favored values of the acyl group RCO— are those derived from alkanoic acids having up to 7 carbon atoms, and substituted alkanoic acids such as phenylpropionic acid, chloracetic acid. Preferred values of R are benzyl and phenoxymethyl.

The process produces 6-amino-2,2-dimethyl-3-(5-tetrazolyl)penams (compounds of formula I), and especially compounds of formula I wherein $R_1$ and $R_2$ are each hydrogen, of high quality and high yield. It further affords a convenient method for improving the quality of 6-amino-2,2-dimethyl-3-(5-tetrazolyl)penams prepared from 6-aminopenicillanic acid by the process described below and which contain various impurities such as penicilloic acids and polymeric-like substances which arise from polymerization of certain blocking groups, such as p-methoxybenzyl and p-hydroxybenzyl following their removal from the tetrazolyl moiety, and by unreacted starting material.

DETAILED DESCRIPTION OF THE INVENTION

The process of this invention when applied to compounds of formula II wherein $R_1$ and $R_2$ are other than hydrogen is conducted by reacting the appropriate compound of formula II in a reaction-inert solvent under anhydrous conditions at a temperature below about —20° C. with a suitable halogenating agent in the presence of an acid binding agent to form an imino halide. Representative solvents are chloroform, methylene chloride, 1,2-dichloroethane benzene, tetrahydrofuran, dimethyl ether of ethylene glycol, nitromethane, diethylether, isopropylether, etc. Suitable halogenating agents are phosphorous pentachloride, phosphorous pentabromide, phosphorous trichloride, phosphorous tribromide, phosphorous oxychloride, phosgene, p-toluenesulfonyl chloride, oxalyl chloride, etc.

Representative acid binding amines are tertiary amines such as dimethylaniline, quinoline, lutidine, pyridine.

The imino chloride, the preferred form of imino halide, is converted to a corresponding imino ether by treatment with a primary alcohol at a temperature between about —20° and about —60° C, and preferably at about —40° C., under anhydrous conditions. Suitable alcohols are alkanols of from 1 to 12 carbon atoms, and preferably of from 1 to 4 carbon atoms, phenylalkanols having from 1 to 7 carbon atoms in the alkanol moiety; alkanediols having from 2 to 6 carbon atoms; alkoxyalkanols having from 2 to 6 carbon atoms; and others such as are enumerated in U.S. Pat. No. 3,499,909. Representative alcohols are methanol, ethanol, propanol, n-butanol, amyl alcohol, decanol, benzyl alcohol, β-phenylethanol, 3-phenyl-1-propanol, 1,3-propanediol, 1,6-hexanediol, 1,2-methoxyethanol, 2-butoxyethanol. The preferred alcohols are methanol, ethanol, propanol, and butanol. Silyl groups, if present on the tetrazolyl moiety as protecting groups, are also removed in this step.

The imino ether is then cleaved by mild hydrolysis with water in the presence of an acid catalyst such as phosphoric acid or hydrochloric acid.

When $R_1$ or $R_2$ of the tetrazolyl moiety is hydrogen, it is protected by replacing it with a tetrazolylpenam nitrogen protecting group as defined herein. A preferred protecting group is trialkylsilyl since such group is easily substituted onto the tetrazolyl moiety and is readily removed under mild conditions as is described herein.

Each of $R_1$ and $R_2$ is defined inter alia as trialkylsilyl having from one to four carbon atoms per alkyl group, alkanoyloxymethyl having from three to eight carbon atoms, 1-alkanolyloxyethyl having from four to nine carbon atoms, triphenylmethyl, substituted triphenylmethyl and phthalidyl. $R_1$ is further defined as a tetrazolylpenam nitrogen protecting group. It is intended by this term to connote all groups known, or obvious, to one skilled in the art, which can be used (a) to permit the synthesis of compounds of formula I and II by the processes described hereinafter, and (b) can be removed under conditions which leave the β-lactam ring system substantially intact.

The nature of the tetrazolylpenam nitrogen protecting group is not critical to this invention. It is its ability to perform a specific function rather than its structure which is important. The selection and identification of appropriate protecting groups can readily and easily be made by one skilled in the art. The suitability and effectiveness of a group as a tetrazolylpenam nitrogen protecting group in this invention are determined by employing a compound of formula II wherein $Y_1$ is the ($R_1$-substituted)-5-tetrazolyl-moiety in question as reactant in the herein-described process for making formula I compounds.

As one skilled in the art will recognize, the variables $R_1$ and $R_2$ when defined as alkanoyloxymethyl, 1-alkanoyloxyethyl and phthalidyl are, in a sense, tetrazolylpenam nitrogen-protecting groups. However, such groups cannot be removed without substantial degradation of the β-lactam ring and, thus, fail to meet the criteria set forth above for a "tetrazolylpenam nitrogen protecting group." They are, however, referred to herein as "pseudo blocking groups."

Examplary of tetrazolylpenam nitrogen protecting groups are:

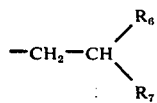

wherein $R_6$ is an electron-withdrawing group, and $R_7$ is either hydrogen or a further electron-withdrawing group, which can be the same as or different from $R_6$.

The function of the electron-withdrawing groups is to render the hydrogen atom on the adjacent carbon atom sufficiently acidic that the protecting group is removable in a retrograde Michael reaction. Such a reaction is well-known in the art. (e.g. House, "Modern Synthetic Reactions," W. A. Benjamin, Inc., New York/Amsterdam, 1965, page 207). Typical electron-withdrawing groups are cyano, alkoxycarbonyl having from two to seven carbon atoms, phenoxycarbonyl, alkylsulfonyl having from one to six carbon atoms, phenylsulfonyl and $SO_2NZ_1Z_2$ wherein $Z_1$ and $Z_2$ are each selected from the group consisting of hydrogen, alkyl having from one to four carbon atoms, phenyl and benzyl. A particularly convenient configuration for this protecting group is that wherein $R_7$ is hydrogen; and preferred values for $R_6$ are alkoxycarbonyl having from two to seven carbon atoms and phenylsulfonyl.

A further tetrazolylpenam nitrogen protecting group which can be used is a group of formula $C(=O)-OR_8$. Such a group can be removed by mild hydrolysis, such as mild alkaline hydrolysis, or by treatment with nucleophile, such as an amine, a thiol or thiolate anion. Although a wide variety of such groups known in the art can be used, particularly convenient are those wherein $R_8$ is alkyl having from one to six carbon atoms, benzyl, phenyl or substituted phenyl, for example, phenyl substituted by up to two moieties each selected from one to four carbon atoms and alkoxy having from one to four carbon atoms.

A still further tetrazolylpenam nitrogen protecting group which can be used is a grouping of formula $-SO_2-R_8$. Such a group is also removed by hydrolysis, or by treatment with a nucleophilic agent, as indicated for the group $C(=O)-O-R_8$, and convenient values for $R_8$ are also alkyl having from one to six carbon atoms, benzyl, phenyl, and substituted phenyl, for example, phenyl substituted by up to two moieties each selected from the group consisting of nitro, fluoro, chloro, bromo, alkyl having from one to four carbon atoms and alkoxy having from one to four carbon atoms.

Another tetrazolylpenam nitrogen protecting group which can be used is

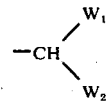

wherein $W_1$ is phenyl, substituted phenyl, furyl, substituted furyl, thienyl or substituted thienyl, and $W_2$ is hydrogen, alkyl, phenyl, substituted phenyl, furyl, substituted furyl, thienyl or substituted thienyl, When $W_1$ is phenyl or substituted phenyl, and $W_2$ is hydrogen, alkyl, phenyl or substituted phenyl, this group can be removed by hydrogenolysis. This group can also be removed by solvolysis in trifluoroacetic acid, when the combined effect of $W_1$ and $W_2$ is sufficient to offer the requisite degree of stability to the incipient carbonium ion.

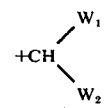

Particularly preferred configurations for this protecting group which afford satisfactory yields of compounds of formula I and are readily removed, are (a) those wherein $W_2$ is hydrogen or alkyl having from one to six carbon atoms, and $W_1$ is phenyl or phenyl substituted with up to two groups selected from the group consisting of hydrogen, hydroxy, nitro, fluoro, chloro, bromo, iodo, alkyl having from one to six carbon atoms, alkoxy having from one to six carbon atoms, alkanoyloxy having from two to seven carbon atoms, formyloxy, alkoxymethoxy having from two to seven carbon atoms, phenyl, and benzyloxy; and (b) those wherein $W_2$ is hydrogen or methyl, and $W_1$ is furyl, 5-methylfuryl, thienyl, or 5-methylthienyl.

Yet still another tetrazolylpenam nitrogen protecting group which can be used is phenacyl or substituted phenacyl. Such a group is removed by reaction with a nucleophilic reagent, such as thiophenoxide. Typical phenacyl groups which can be used are those of formula

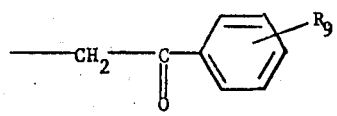

wherein $R_9$ is selected from the group consisting of hydrogen, nitro, fluoro, chloro, bromo, and phenyl.

Highly useful substituent groups for the 5-tetrazolyl moiety $Y_1$ when $R_1$ or $R_2$ is hydrogen are silyl groups, particularly those derived from silylating agents selected from the group consisting of

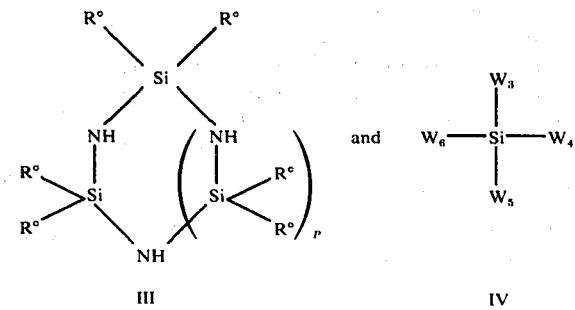

III                    IV wherein $W_3$ is selected from the group consisting of halogen and $W_4$ and each of $W_4$ and $W_5$ is selected from the group consisting of hydrogen, alkyl of from one to four carbon atoms, phenyl, benzyl, tolyl and dimethylaminophenyl, at least one of the said W's being other than halogen and hydrogen; $R°$ is alkyl of 1 to 7 carbon atoms; p is an integer from 1 to 2; and $W_6$ is selected from the group consisting of halogen and

and and $W_7$ is selected from the group consisting of hydrogen and alkyl of 1 to 7 carbon atoms; and $W_8$ is selected from the group consisting of hydrogen, alkyl of 1 to 7 carbon atoms and

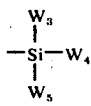

The silyl groups are introduced into the tetrazolyl moiety by methods known to those skilled in the art. The silylation reaction is conducted in an anhydrous reaction-inert, that is, an anhydrous, non-hydroxylic solvent of the type mentioned above, and preferably in methylene chloride, at a temperature of from about −10° to about −80° C., and preferably at from −20° to −60° C. The reaction is often conducted in the presence of an acid-binding agent, that is, a base such as an alkali metal carbonate or tertiary amine, e.g., diethylaniline, pyridine, quinoline, and lutidine. The base may be a part of the silylating agent as is the case when the silylating agent is of formula IV wherein $W_6$ is —$NW_7W_8$ of formula III, and said agent is used in combination with a compound of formula IV wherein $W_6$ is halogen. Representative of suitable silylating agents are those disclosed in U.S. Pat. No. 3,499,909 such as trimethylchlorosilane, hexamethyldisilazane, triethylchlorosilane, methyltrichlorosilane, dimethyldichlorosilane, triethylbromosilane, tri-n-propylchlorosilane, bromomethyldimethylchlorosilane, tri-n-butylchlorosilane, methyldiethylchlorosilane, dimethylethylchlorosilane, phenyldimethylbromosilane, benzylmethylethylchlorosilane, phenylethylmethylchlorosilane, triphenylchlorosilane, triphenylfluorosilane, tri-o-tolychlorosilane, tri-p-dimethylaminophenylchlorosilane, N-ethyltriethylsilylamine, hexaethyldisilazane, triphenylsilylamine, tri-n-propylsilylamine, tetraethyldimethyldisilazane, tetramethyldiethyldisilazane, tetramethyldiphenyldisilazane, hexaphenyldisilazane, hexa-p-tolyldisilazane, etc., and mixtures of these. The same effect is produced by hexa-alkylcyclotrisilazanes or octaalkylcyclotetrazilazanes. Other suitable silylating agents are silylamides and silylureides, such as trialkylsilylacetamide and a bis-trialkylsilylacetamide as is disclosed in U.S. Pat. No. 3,499,909.

The preferred silylating agents are dimethyldichlorosilane, chlorosilane and hexamethyldisilazane, and especially mixtures of these because of their overall reactivity, availability, ease of handling, satisfactory yields produced and, as regards the mixtures, the generation of ammonia by the disilazane which serves as acid-binder. The procedures illustrated herein are those described by Pierce in "Silylation of Organic Compounds," Pierce Chemical Company, Rockford, Illinois.

The favored tetrazolylpenam nitrogen protecting groups are those which can be removed by other than acid conditions. Acid conditions are generally avoided in order to prevent or minimize degradation of the β-lactam upon removal of the protecting group from a compound of formula I. Illustrative of such protecting groups are those removable by such means as hydrogenolysis ($R_1$ is benzyl or substituted benzyl), treatment with a base ($R_1$ is p-hydroxybenzyl), or a substituted silyl group ($R_1$ or $R_2$ is trialkylsilyl).

The term "tetrazolylpenam nitrogen protecting group" is intended, in the most general sense, to cover those groups which protect the tetrazole ring during or after formation thereof and during reaction of the so-protected tetrazolylpenam compounds. A group can, therefore, be regarded as tetrazolylpenam nitrogen protecting group when it (a) can be attached to the tetrazolyl group during or after formation thereof; (b) will permit reaction of the C-6 acylamido group of the tetrazolylpenam; and (c) can be removed from the tetrazolyl moiety of compounds of formulae I or II without substantial degradation of the tetrazolylpenam ring system. Illustrative of such groups, in addition to those specifically enumerated herein as tetrazolylpenam nitrogen protecting groups are trialkylsilyl, triphenylmethyl, and substituted triphenylmethyl groups.

The products of formula I are recovered by standard procedures. For example, when $R_1$ and $R_2$ of formula I are hydrogen, 6-amino-2,2-dimethyl-3-(5-tetrazolyl)penam is recovered by adjusting the pH of the reaction mixture to about 4.2, the isolectric point, to precipitate the product. When $R_1$ is p-methoxybenzyl, the product is recovered by adding n-hexane to the imino ether containing reaction mixture to force the product out of solution.

The crude product is separated, washed with hexane and then dissolved in a suitable solvent, e.g. methylene chloride. The solution is washed with brine, dried and evaporated under reduced pressure to give the product.

PREPARATION OF STARTING MATERIALS

The starting materials (formula II) for this process are prepared by the acylation of a 6-amino-2,2-dimethyl-3-(5-tetrazolyl)penam (formula I) by the reaction sequence described below:

In the first step, 6-(triphenylmethylamino)penicillanic acid (Sheehan et al., J. Am. Chem. Soc. 81, 5838, 1959) is converted into an amide of formula

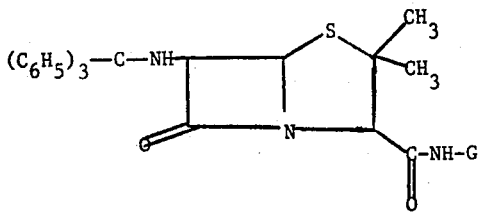

wherein G is selected from the group consisting of —C(=O)—O—$R_8$, —$SO_2$—$R_8$, $CH_2CH_2R_6$ wherein $R_8$ and $R_6$ are as previously defined; and —$CHW_1W_2$, particularly the preferred configurations thereof defined above.

In the case wherein G is —$CH_2CH_2R_6$ or —$CHW_1W_2$ the amide is prepared by activation of the 3-carboxy group of 6-(triphenylmethylamino)penicillanic acid, e.g. by mixed anhydride formation, followed by reaction with an equimolar proportion of amine of formula $NH_2CH_2CH_2R_6$ or $H_2N$—$CHW_1W_2$. Thus, formation of the mixed anhydride involves reacting an appropriate carboxylate salt of 6-triphenylmethylaminopenicillanic acid in a reaction-inert organic solvent, with approximately equimolar proportions of pivaloyl chloride or lower-alkyl chloroformates. Appropriate salts are, for example, alkali metal salts, such as sodium or potassium salts, and amine salts, such as triethylammonium, pyridinium, N-ethylpiperidinium or N,N-dimethylanilinium salts. Suitable solvents are chlorinated hydrocarbons, such as chloroform, methylene chloride; aromatic hydrocarbons, such as benzene, toluene and xylene; and ethers, such as diethyl ether, tetrahydrofuran and 1,2-dimethoxyethane. The reaction is usually carried out at a temperature of from about −50° to about 30° C., and preferably at about 0° C. and is complete in about one hour. The product is isolated simply by filtering off the insoluble materials, and then evaporating the solvent in vacuo to give the crude anhydride. The mixed anhydride product need not be isolated. It can be used in situ for reaction with the amine simply by contacting the reactants in an inert solvent, for about 0.5 to about 2.0 hours, at a temperature in the range from about −30° to about 3° C. and preferably at around 0° C. The same solvents identified above for mixed anhydride formation are useful for the instant reaction.

When this reaction is conducted in a water-immiscible solvent, the product is usually isolated by washing the reaction mixture with water and then concentrating the organic solvent to dryness in vacuo, to give the crude product. The latter product can be used immediately for Step 2, or, if desired, it can be purified further by well-known methods. It is sometimes convenient simply to wash the reaction mixture with water, and then use the so-produced solution of amide directly in Step 2.

In the case wherein G is —C(=O)—O—$R_8$ or —$SO_2R_8$, the amide of formula V is prepared by reaction of 6-(triphenylmethylamino)penicillanic acid with the appropriate isocyanate of formula $R_8$—O—C(=O)—N=C=O or $R_8$—$SO_2$—N=C=O. The reaction is usually carried out by contacting substantially equimolar quantities of the reactants, in a reaction inert organic solvent, at a temperature in the range from about 0° to about 30° C., for a period of from about one hour to about twenty hours. The product can be isolated simply by removal of the solvent in vacuo or the solution of the amide can be used in situ for Step 2. The isocyanates of formula $R_8$—O—(C=O)—N=C=O are prepared by reaction of a carbamate of formula $R_8$—O—C(=O)—$NH_2$ with oxalyl chloride.

In Step 2, the product from Step 1, or a simple transformation product thereof in which any phenolic hydroxy groups are protected by conversion to formyloxy, alkanoyloxy, or alkoxymethyl groups, is converted into an imidoyl chloride by reacting the said amide in a reaction-inert organic solvent with phosgene and a tertiary amine. About one molar equivalent of phosgene is usually used, but amounts up to about two or three molar equivalents are sometimes employed. The tertiary amine is preferably present in an amount equal to or greater than the amount of phosgene. The reaction is carried out at a temperature in the range from about −20° to about 30° C., and preferably at about 25° C. It usually requires a few hours to reach completion. A variety of tertiary amines can be used in this process, for example trimethylamine, triethylamine, N,N-dimethylaniline, N-methylmorpholine and pyridine. Typical solvents which can be used are chlorinated hydrocarbons, such as chloroform, methylene chloride and 1,2-dichloroethane, and ethers such as tetrahydrofuran and 1,2-dimethoxyethane. If desired, the imidoyl chloride can be isolated by evaporation of the filtered reaction mixture, but in many instances it is convenient to use the imino chloride in situ.

Several other reagents, for example, thionyl chloride or a phosphorous halide such as phosphorous pentachloride are operative in the imidoyl chloride forming reaction. Moreover, if desired, use can be made of the corresponding imidoyl bromide.

In Step 3 of the process, the above imidoyl chloride is converted into a tetrazolylpenam compound of formula VI

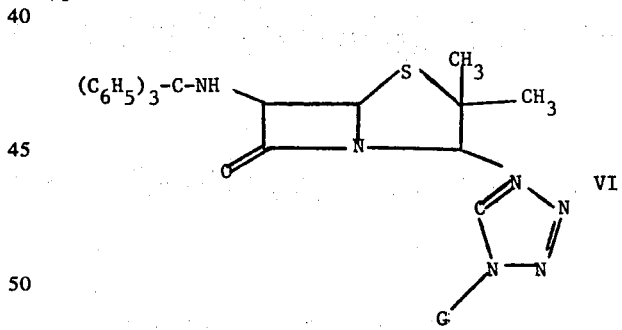

wherein G is as previously defined. This transformation comprises treating the said imidoyl chloride in an reaction-inert solvent with about one molar equivalent, or sometimes a small excess, of azide ion. The reaction mixture is then stored at or about ambient temperatures for several hours, for example, overnight, until conversion into tetrazole is substantially complete. A wide variety of azide ion sources such as trimethylsilyl azide, triethylsilyl azide, potassium and sodium azide, tributylammonium azide, N,N-dimethylanilinium azide, N-methylmorpholinium azide and pyridinium azide; tetramethylguanidinium azide are operative in this process. Appropriate solvents in cases wherein the azide ion source is a trialkylsilyl azide or a trisubstituted ammonium azide are chloroform, methylene chloride, 1,2-dichloroethane and dipolar aprotic solvents such as N-methylpyrrolidone. In reactions where a metal salt of hydrazoic acid constitutes the azide ion source, dipolar aprotic solvents become the solvent-type of choice. Product isolation is achieved using standard methods. When a low boiling chlorinated hydrocarbon is the solvent, the reaction mixture is washed with dilute alkali and then the organic solvent is evaporated off. When a dipolar aprotic solvent is the solvent, the reaction mixture is diluted with a large excess of dilute alkali, and then after appropriate adjustment of the pH, the product is isolated by solvent extraction.

The N-triphenylmethyl derivatives thus obtained are converted to compounds of formula I by treatment with an acid such as methanesulfonic acid, benzenesulfonic acid, p-toluenesulfonic acid, hydrogen chloride, hydrogen bromide, acetic, propionic, chloroacetic or trifluoroacetic acid. The reaction is normally carried out by dissolving the starting material in an appropriate solvent and adding about two molar equivalents of the acid reagent at or about ambient temperature. Reaction is complete within about 1 hour, and the product is present in the reaction medium in the form of the acid-addition salt corresponding to the acid reagent used. Appropriate solvents are diethyl ether, tetrahydrofuran, dioxane, 1,2-dimethoxyethane, chloroform, methylene chloride, 1,2-dichloroethane, acetone, methyl ethyl ketone, ethyl acetate, butyl acetate, hexane, cyclohexane, benzene, methanol, ethanol, and butanol. A favored procedure comprises the use of p-toluenesulfonic acid in acetone since the p-toluenesulfonate salt of the product often precipitates.

The compounds of formula I are then converted to acyl derivatives of formula II by acylation with an activated derivative of a carboxylic acid, such as an acid chloride, a mixed anhydride, an activated ester or the reactive intermediate formed by the acid and dicyclohexylcarbodiimide or other peptide bond forming reagent. A typical acylation procedure comprises reacting a compound of formula I in a reaction inert solvent, e.g. methylene chloride, chloroform, tetrahydrofuran, ethyl acetate, butyl acetate, acetone, methyl ethyl ketone, or N,N-dimethylformamide, with an equimolar amount of an appropriate acid chloride, preferably phenacetyl chloride or phenoxyacetyl chloride, at a temperature of from about −40° to about 30° C. and preferably from about −10° to about 10° C. The product is isolated by standard methods as by evaporation of the reaction mixture to dryness and treatment of the residue with a water-immiscible solvent and water. The acylated product if insoluble, is filtered off; otherwise the pH of the aqueous phase is adjusted to an appropriate value and the phase containing the product separated and evaporated.

Alternatively, when $R_1$ and $R_2$ are hydrogen, the acid halide is added to a solution of the formula I reactant in water-water miscible solvent at a temperature of from about 10° to about 30° C. The pH is maintained at from about 6 to about 8 by addition of sodium or potassium hydroxide. The product is isolated by known procedures.

In the mixed anhydride acylation procedure, the anhydride of the appropriate carboxylic acid and a lower alkylchloroformate, e.g. ethyl chloroformate, is reacted with the appropriate formula I compound in a 1:1 molar ratio in a reaction-inert solvent such as are enumerated above at a temperature of from about −10° to 30° C., preferably at −10° to 0° C. The products are isolated as described above and by other methods known to those skilled in the art. When $R_1$ and $R_2$ are hydrogen, the reaction is normally conducted in the presence of an equimolar amount of a tertiary amine, suc as triethylamine.

Another variation of acylation, comprises conversion of the appropriate carboxylic acid to an active ester such as p-nitrophenyl, 2,4,6-trichlorophenyl, thiol phenyl, thiol methyl,N-hydroxysuccinimide and N-hydroxyphthalimide esters, followed by treatment with a compound of formula I or a salt thereof. The acylation is conducted by dissolving the active ester and formula I compound, or a salt thereof, in a dipolar aprotic solvent such as N,N-dimethylformamide, N,N-dimethylacetamide or N-methylpyrrolidone. The solution is stored at about ambient temperature for several hours, for example overnight, and then the product is isolated by standard methods.

A still further acylation comprises contacting the appropriate compound of formula I with a carboxylic acid in the presence of certain agents known in the art for forming peptide bonds. Such agents include carbodiimides, for example, dicyclohexylcarbodiimide and 1-ethyl-3-(3-dimethylaminopropyl)carbodiimide, methoxyacetylene and N-ethoxycarbonyl-2-ethoxy-1,2-dihydroquinoline. The reaction is carried out in a solvent such as acetonitrile, N,N-dimethylformamide or N-methlypyrrolidone.

Implicit in the above procedures when conducted in non-aqueous systems, is the observation that in a process for the acylation of a compound of formula I, hydrogen substituents located at $R_1$, $R_2$ or on the 6-amino group can be replaced by tri(lower-alkyl)silyl substituents. Said tri(lower-alkyl)silyl substituents are then removed and replaced by hydrogen at the end of the acylation by brief exposure of the product to a protic solvent system, such as water or a lower-alkanol, for example methanol or ethanol. By virtue of its availability, the trimethylsilyl group is a preferred member. It can be introduced into the starting formula I compound by methods well known in the art, such as, for example, using trimethylchlorosilane or N-trimethylsilylacetamide, as discussed by Birkofer and Ritter in Angewandte Chemie (International Edition in English), 4, 417–418 and 426 (1965).

Compounds of formula II wherein $R_1$ and $R_2$ of the 5-tetrazolyl moieties are hydrogen, alkanoyloxymethyl, 1-alkanoyloxyethyl or phthalidyl are useful antibacterial agents. Compounds of formula I wherein $R_1$ and $R_2$ are triphenylmethyl, and those wherein $R_1$ is a tetrazolylpenam nitrogen protecting group as defined herein are intermediates for the production of 6-acylamido-2,2-dimethyl-3-(5-tetrazoyl)penams wherein $R_1$ and $R_2$ are hydrogen, alkanoyloxymethyl, 1-alkanoyloxyethyl or phthalidyl. Removal of the triphenylmethyl, substituted triphenylmethyl and tetrazolylpenam nitrogen protecting groups by known methods affords the corresponding compounds wherein $R_1$ and $R_2$ are hydrogen. Acylation of the 6-amino group of the resulting compounds and, if desired, alkylation of the tetrazolyl moieties ($R_1=R_2=H$) by reaction with alkanoyloxymethyl, 1-alkanoyloxyethyl or phthalidyl chlorides (or bromides) affords bactericidally active compounds.

The 6-acylamido-2,2-dimethyl-3-(5-tetrazolyl)penams of formula II are valuable antibacterial agents in vitro and in vivo against a wide variety of gram-positive and gram-negative bacteria. Their useful activity can readily be demonstrated by in vitro tests against various organisms in a brainheart infusion medium by the usual two-fold serial dilution technique. Their in vitro activity renders them useful for topical application in the form of ointments, creams and the like, or for sterilization purposes, e.g. sick-room utensils. They are also effective antibacterial agents in vivo in animals, including man, not only via the parenteral route of administration but also by the oral route of administration. The oral and parenteral dosage levels for the herein described compounds are, in general, on the order of up to 200 mg./kg. and 100 mg./kg. of the body weight per day, respectively.

For such purposes, the pure materials or mixtures thereof with other antibiotics can be employed. They may be administered alone or in combination with a pharmaceutical carrier on the basis of the chosen route of administration and standard pharmaceutical practice. For example, they may be administered orally in the form of tablets containing such excipients as starch, milk sugar, certain types of clay, etc. or in capsules alone or in admixture with the same or equivalent excipients. They may also be administered orally in the form of elixirs or oral suspensions which may contain flavoring or coloring agents, or be injected parenterally, that is, intramuscularly or subcutaneously. For parenteral administration, they are best used in the form of a sterile aqueous solution which may be either aqueous such as water, isotonic saline, isotonic dextrose, Ringer's solution, or non-aqueous such as fatty oils of vegetable origin (cotton seed, peanut oil, corn, sesame) and other non-aqueous vehicles which will not interfere with the therapeutic efficiency of the preparation and are non-toxic in the volume or proportion used (glycerol, propylene glycol, sorbitol). Additionally, compositions suitable for extemporaneous preparation of solutions prior to administration may advantageously be made. Such compositions may include liquid diluents, for example propylene glycol, diethyl carbonate, glycerol, sorbitol, etc.; buffering agents, as well as local anesthetics and inorganic salts to afford desirable pharmacological properties.

Illustrative examples of the process of this invention and representative preparations for making the necessary starting materials are provided below.

EXAMPLE I

6-Amino-2,2-Dimethyl-3-(5-Tetrazolyl)penam

To a flame-dried flask equipped with a magnetic stirrer, thermometer and drying tube is added 10 ml. of methylene chloride, 0.716g. of 6-(2-phenylacetamido)-2,2-dimethyl-3-(5-tetrazolyl)penam and 0.630g. of N,N-dimethylaniline at room temperature. Chlorotrimethylsilane (0.382 ml.) is then added and the reaction mixture cooled in a dry ice-acetone bath to -50° C. To the clear, off-white solution is added 0.456g of phosphorous pentachloride in one portion and the resulting mixture stirred at -35° to -45° C. for 2 hours. It is then cooled to -60° C. and continuously stirred while 3.5g. of n-butyl alcohol is added by syringe through a serum stopper. The temperature, which rises to -50° C. upon the alcohol addition, is allowed to rise to -40° C. and stirring continued for 2 more hours. The reaction mixture is then transferred to a beaker, 3 ml. of water added and the pH adjusted to 4.5 with sodium bicarbonate and then to 4.2 by means of 5% hydrochloric acid. The mixture is chilled and the tan precipitate filtered off, washed with ether and dried in vacuo to give 0.235 g. (48.9% Yield) of product. M.P. 186° C. (dec.).

Repetition of this procedure but replacement of phosphorous pentachloride by an equivalent amount of phosphorous pentabromide, phosphorous oxychloride, phosgene, or phosphorous tribromide, affords the same product.

The chlorotrimethylsilane when replaced by dichlorodimethylsilane in the above procedure affords the same product.

EXAMPLE II

6-Amino-2,2-Dimethyl-3-(1-[p-Methoxybenzyl]tetrazol-5-yl)Penam Hydrochloride A flame-dried flask is charged with 5.0 ml. of methylene chloride, 494 mg. of 6-(2-phenoxyacetamido)-2,2-dimethyl-3-(1-[p-methoxybenzyl]tetrazol-5-yl)penam and 275 mg. of freshly distilled quinoline. The resulting solution is stirred and cooled in a dry-ice acetone bath to -25° C. Phosphorous pentachloride (228 mg.) is added all at once to the reaction mixture which is then stirred at from -25° to -20° C. for 4 hours. The mixture is then cooled to -30° C., 600 mg. of n-propanol is rapidly added dropwise and the reaction mixture is stirred for 1 hour at -25° to -20° C. It is then treated with 4 ml. of brine and rapidly stirred while being allowed to warm to room temperature. Hexane (60 ml.) is slowly added dropwise to the reaction mixture during the warming stage. The orange oil which separates is recovered by decantation of the organic solution and is washed twice with hexane. It is then dissolved in methylene chloride, the resulting solution washed once with brine and evaporated under reduced pressure to give 360 mg. (94% yield) of product as an off-white foam.

Repitition of the above procedure, but substituting an equivalent amount of phosphorous oxychloride, phosphorous pentabromide, or p-toulenesulfonylchloride for phosphorous pentachloride produces the same product.

EXAMPLE III

6-Amino-2,2-dimethyl-3-(2-[pivaloyloxymethyl]tetrazol-5-yl)penam

To a stirred solution of 0.932 g. (7.21 m mole) of quinoline in 8.0 ml. of chloroform is added 0.840 g. (4.05 m mole) of phosphorus pentachloride. The suspension is cooled to -15° C., and then 1.81 g. (3.84 m mole) of 6-(2-phenylacetamido)-2,2-dimethyl-3-(2-[pivaloyloxymethyl]tetrazol-5-yl) penam is added. Stirring is continued for a further 30 minutes, at ca. -5° C, and then 2.15 g. (35.7 m mole) of n-propanol is added. Stirring is continued for a further 30 minutes, again at ca. -5° C., and then 25 ml. of 90:10 isopropyl ether-acetone is added, followed immediately by a solution of 1.35 g. of sodium chloride in 6.02 ml. of water. The temperature rises to 15° C. and then it is lowered again to -15° C. The precipitate which has formed is filtered off and dried, giving 1.33 g. (88% yield) of 6-amino-2,2-dimethyl-3-(2-[pivaloyloxymethyl]tetrazol-5-yl)penam hydrochloride. The infrared spectrum (KBr disc) shows absorptions at 1785 cm$^{-1}$ ($\beta$-lactam) and 1750 cm$^{-1}$ (ester). The NMR spectrum (DMSO-d$_6$) shows absorptions at 6.70 ppm (singlet, 2H, pivaloyloxymethylene hydrogens), 5.75 ppm (doublet, 1H, C-5 hydrogen), 5.50 ppm (singlet, 1H, C-3 hydrogen), 5.70 ppm (doublet, 1H, C-6 hydrogen), 1.75 ppm (singlet, 3H, C-2 methyl hydrogens), 1.20 ppm (singlet, 9H, t-butyl hydrogens) and 1.10 ppm (singlet, 3H, C-2 methyl hydrogens).

EXAMPLE IV

6-Amino-2,2-dimethyl-3-(1-[pivaloyloxymethyl]tetrazol-5-yl)penam

The title compound is prepared as its hydrochloride, in 90% yield, from 6-(2-phenylacetamido)-2,2-dimethyl-3-(1-[pivaloyloxymethyl]tetrazol-5-yl)penam, using the method of Example III. The infrared spectrum (KBr disc) shows absorptions at 1780 cm$^{-1}$ ($\beta$-lactam) and 1740 cm$^{-1}$ (ester). The NMR spectrum (DMSO-d$_6$) shows absorptions at 6.71 ppm (singlet, 2H, pivaloyloxy methylene hydrogens), 5.88 ppm (singlet, 1H, C-3 hydrogen), 5.83 ppm (doublet, 1H, C-5 hydrogen), 5.20 ppm (doublet, 1H, C-6 hydrogen), 1.80 ppm (singlet, 3H, C-2 methyl hydrogens), 1.20 ppm (singlet, 9H, t-butyl hydrogens) and 1.16 ppm (singlet, 3H, C-2 methyl hydrogens).

EXAMPLE V

6-Amino-2,2-Dimethyl-3-(5-tetrazolyl)penam

The procedure of Example I is repeated but using 6-(2-phenoxyacetamido)-2,2-dimethyl-3-(5-tetrazolyl)penam as reactant in place of the analogous 6-phenylacetamido compound to produce the title compound.

EXAMPLE VI

6-Amino-2,2-Dimethyl-3-(1-[p-Methoxybenzyl]tetrazol-5-yl)penam Hydrochloride

Following the procedure of Example II but using 6-(2-phenylacetamido)-2,2-dimethyl-3-(1-[p-methoxybenzyl]tetrazol-5-yl)penam in place of the corresponding 6-phenoxyacetamido compound as reactant affords the title porduct.

In like manner the 6-(2-arylacetamido)-2,2-dimethyl-3-(1-[substituted]tetrazol-5-yl)penams of Preparations DD-JJ are converted to the corresponding 6-amino-2,2-dimethyl-3-(1[substituted]tetrazol-5-yl)penams.

EXAMPLE VII

The procedure of Example III is repeated but using as reactant in place of 6-(2-phenylacetamido)-2,2-dimethyl-3-(2-[pivaloyloxymethyl]tetrazol-5-yl)penam, the alkanoyloxymethyl derivatives of Preparation X to produce, in each instance, the corresponding 6-amino-2,2-dimethyl-3-([substituted]tetrazol-5-yl)penams wherein the substituent is alkanoyloxyalkyl or phthalidyl.

EXAMPLE VIII

The procedure of Example I using PCl$_5$ as halogenating agent is repeated but substituting the n-butyl alcohol used therein for imino ether formation by the following alcohols:

| | |
|---|---|
| methyl | 4-hydroxybutyl |
| n-propyl | 6-hydroxyhexyl |
| n-hexyl | 2-isopropoxyethyl |
| 1-dodecyl | 2-(p-chlorophenoxy)ethyl |
| 1-octyl | 2-hydroxyethoxyethyl |
| benzyl | 2-(p-methoxybenzyloxy)ethyl |
| 2-phenethyl | 4-methoxy butyl |

-continued

| | |
|---|---|
| 3-phenylpropyl | 2-phenoxyethyl |
| 2-methoxyethyl | 4-phenoxybutyl |

PREPARATION A 6-(Triphenylmethylamino)-2,2-dimethyl-3-(1-[4-methoxybenzyl]tetrazol-5-yl)penam A. 6-(Triphenylmethylamino)-2,2-dimethyl-3-(N-[4-methoxybenzyl]carbamoyl)penam To a stirred slurry of 86.4 g. (0.8 mole) of 6-aminopenicillanic acid in 600 ml. of anhydrous chloroform is added 11.2 ml. (0.4 mole) of triethylamine, and the mixture is stirred at ambient temperature until a clear solution is obtained (ca. 15 minutes). To this solution is then added, portion-wise over about 25 minutes, 134.9 g. (0.44 mole) of 90% pure triphenylmethyl chloride, at ambient temperature. Stirring is continued for a further 64 hours, and then 5.6 ml. of triethylamine is added. The solution is cooled to 0°–5° C., and then an ice-cold solution of 38 1. (0.4 mole) of ethyl chloroformate in 80 ml. of cloroform is added dropwise during 30 minutes with the reaction temperature being maintained between 4° and 9° C. After a further 15 minutes of stirring, 52.4 ml. (0.4 mole) of 4-methoxybenzylamine is injected into the reaction medium, below the surface of the solvent, at 4° to 9° C., and over a period of 30 minutes. Stirring is continued for a further 30 minutes at 3° to 6° C., for 20 minutes while the reaction medium warms to 20° C. The reaction mixture is then washed with water, followed by brine. Finally, it is dried using magnesium sulfate to give a chloroform solution of 6-(triphenylmethylamino)-2,2-dimethyl-3-(N-[4-methylbenzyl]carbamoyl)penam.

B. 6-(Triphenylmethylamino)-2,2-dimethyl-3-(1-[4-methoxybenzyl]tetrazol-5-yl)penam To a chloroform solution containing 69.4 g. (0.120 mole) of 6-(triphenylmethylamino)-2,2-dimethyl-3-(N-[4-methoxybenzyl]carbamoyl)penam, and having a volume of 133.3 ml., prepared by the method described in (A) above, is added a further 132.7 ml. of chloroform, followed by 29.1 ml. (0.360 mole) of pyridine. This solution is cooled to 10° C., and then 26.22 g. (0.126 mole) of phosphorus pentachloride is added during 15 minutes, with stirring. Stirring is continued at ca. 10° C. for 10 minutes, and then at ambient temperature for a further 1.5 hours, giving a solution of the imino chloride. To a one-sixth aliquot of this imino chloride solution is added 4.85 ml. (0.060 mole) of pyridine, followed by 2.42 ml. (0.060 mole) of methanol at ca. 25° C., with stirring. After a further 15 minutes of stirring 2.03 g. (0.038 mole) of ammonium chloride, followed by 2.59 g. (0.039 mole) of 95% pure sodium azide, is added. The reaction mixture is then stirred at ambient temperature for a further 4 hours. At this point, 400 ml. of water and 200 ml. of chloroform are added, and then the layers are separated. The organic phase is washed with water, dried using magnesium sulfate, and then concentrated to a small volume in vacuo. This final chloroform solution is added dropwise with stirring to a large volume of diisopropylether, and, after 30 minutes, the precipitate which has formed is filtered off. This affords 6.1 g. of 6-(triphenylmethylamino)-2,2-dimethyl-3-(1-[4-methoxybenzyl]tetrazol-5-yl)penam. The infrared spectrum of the product (KBr disc) shows an absorption band at 1790 cm$^{-1}$ ($\beta$-lactam); and the NMR spectrum (in CDCl$_3$) shows absorptions at 7.25 ppm (multiplet, aromatic hydrogens), 5.40 ppm (broad singlet, benzyl hydrogens), 5.05 ppm (singlet, C-3 hydrogen), 4.50–4.30 ppm (multiplet, C-5 and C-6 hydrogens), 3.70 ppm (singlet, methoxy hydrogens), 3.50–3.10 ppm (broad peak, NH), 1.50 ppm (singlet, C-2 methyl hydrogens) and 0.75 ppm (singlet, C-2 methyl hydrogens).

PREPARATION B 6-(triphenylmethylamino)-2,2-dimethyl-3-(1-[4-benzyloxybenzyl]tetrazol-5-yl)penam 6-(Triphenylmethylamino)-2,2-dimethyl-3-(N-[4-benzyloxybenzyl]carbamoyl)penam — To a stirred solution of 20.0 g. of 6-triphenylmethylamino-penicillanic acid (Sheehan and Henery-Logan, *Journal of the American Chemical Society*, 81, 5836 [1959]) in 140 ml. of acetone, at 0°–5° C., is added 6.08 ml. of triethylamine followed by 5.78 ml. of isobutyl chloroformate. After a further 10 minutes, the mixture is filtered directly into a stirred solution of 9.28 g. of 4-benzyloxybenzylamine in 1,000 ml. of water and 300 ml. of acetone at ambient temperature. The mixture so obtained is stirred for 4 minutes, and then an additional 500 ml. of water is added. Stirring is continued for a further 7 minutes, and then the reaction mixture is extracted with ether. The ether is dried using anhydrous magnesium sulfate, and then evaporated to dryness in vacuo. The crude product so obtained is re-dissolved in 200 ml. of ether, which is then added dropwise over 10 minutes to 2,500 ml. of hexane. The solid which precipitates is filtered off, giving 21.5 g. of 6-(triphenylmethylamino)-2,2-dimethyl-3-(N-[4-benzyloxybenzyl]carbamoyl)penam.

6-(Triphenylmethylamino)-2,2-dimethyl-3-(chloro-[N-(4-benzyloxybenzyl)imino]methyl)penam — To a stirred solution of 2.0 g. of the above-described amide in 10 ml. of dry chloroform, at 0°–5° C., is added 0.99 ml. of pyridine, followed by 5.42 ml. of a 2.26 M solution of phosgene in chloroform. The reaction mixture is then stirred at ambient temperature overnight. At this point, it is evaporated to dryness in vacuo, yielding a viscous gum, which is extracted with 100 ml. of ether. The ether is filtered, and evaporation of the filtrate affords the imino chloride as a yellow foam.

6-(Triphenylmethylamino)-2,2-dimethyl-3-(1-[4-benzyloxybenzyl]tetrazol-5-yl)penam — The above-described imino chloride is re-dissolved in 8 ml. of dry N,N-dimethylformamide. To this solution is added 249 mg. of potassium azide, and the turbid solution is stirred at ambient temperature for 2.25 hours. The solvent is evaporated at ambient temperature, under high vacuum, leaving a brown gum. This residue is partitioned between 60 ml. of water and 150 ml. of ether. The ether phase is separated off, washed with saturated brine, dried using anhydrous sodium sulfate, and finally evaporated to dryness in vacuo. The residue is 980 mg. of 6-(triphenylmethylamino)-2,2-dimethyl-3-(1-[4-benzyloxybenzyl]tetrazol-5-yl)penam. Its NMR spectrum (in CDCl$_3$) shows absorption bands at 7.30 ppm (multiplet, aromatic hydrogens), 5.45 ppm (quartet, benzyl hydrogens), 5.05 ppm (singlet, C-3 hydrogen), 5.00 ppm (singlet, benzyl hydrogens), 4.40 ppm (multiplet, C-5 and C-6 hydrogens), 1.40 ppm (singlet, C-2 hydrogen) and 0.70 ppm (singlet, C-2 hydrogen).

PREPARATION C 6-(Triphenylmethylamino)-2,2-dimethyl-3-(1-furfuryltetrazol-5-yl)penam A. 6-(triphenylmethylamino)-2,2-dimethyl-3-(N-furfurylcarbamoyl)penam To a stirred slurry of 216 g. (1 mole) of 6-aminopenicillanic acid in 1500 ml. of chloroform, is added, at 25°–30° C., 278 ml. (2 mole) of triethylamine. To the solution thus obtained is added, portionwise during 25 minutes, 306 g. (1.1 mole) of triphenylmethyl chloride, at 25°–30° C. Stirring is then continued for 44 hours at ambient temperature.

A 522-ml. portion (0.25 mole) of the above 6-(triphenylmethylamino)penicillanic acid solution is cooled to 4° C., and then 3.5 ml. of triethylamine is added. With vigorous stirring is then added 23.75 ml. of ethyl chloroformate at 5°–10° C. Stirring is continued for a further 30 minutes at ca. 6° C. at the end of the addition, and then 8.43 ml. of furfurylamine is injected into the reaction medium below the surface of the solvent. At 10 minute intervals, three further portions of furfurylamine (5.90 ml., 4.22 ml. and 3.54 ml.) are then injected into the reaction medium in similar fashion. The total volume of furfurylamine added is 22.09 ml. (0.25 mole), and the temperature is maintained at ca. 6° C. throughout the addition of the amine. When the addition of the amine is complete, the cooling bath is removed and the reaction medium is stirred at ca. 25° C. for 45 minutes. It is then washed successively with three portions of water, and one portion of brine. Finally, it is dried using anhydrous magnesium sulfate. This affords 610 ml. of chloroform solution of 6-(triphenylmethylamino)-2,2-dimethyl-3-(N-furfurylcarbamoyl)penam. The NMR spectrum of this solution showed absorptions at 7.3 ppm (17H, m), 6.2 ppm (1H, m), 4.35 ppm (3H, m), 4.05 ppm (2H, s), 1.6 ppm (3H, s) and 1.35 (3H, s):

B. 6-(triphenylmethylamino)-2,2-dimethyl-3-(1-furyltetrazol-5-yl)penam

To a stirred solution of 3.05 g. (5.7 mmole) of 6-(triphenylmethylamino)-2,2-dimethyl-3-(N-furfurylcarbamoyl)penam, in 8 ml. of chloroform, at 0° C., is added 1.35 ml. (17 mmole) of pyridine, followed by 2.64 ml. of a 4.33 M solution of phosgene in chloroform. Stirring is then continued for 1 hour at 25° C. The chloroform, and excess phosgene and pyridine, are then removed by evaporation in vacuo, and the residue is redissolved in 5 ml. of chloroform. The solution is cooled to 0° C., and then 2.25 g. (14.4 mmole) of tetramethylguanidinium azide is added in several small portions. Stirring is continued for 15 minutes at ambient temperature, and then 20 ml. of chloroform, followed by 30 ml. of water, are added and the pH is adjusted to 6.5. The chloroform layer is separated off, washed with water, followed by brine, and then dried (MgSO$_4$). Removal of the solvent by evaporation in vacuo leaves 3.37 g. of a dark-red foam. The foam is re-dissolved in a small volume of chloroform and absorbed onto a column of chromatographic silica gel. Elution of the column with chloroform, followed by evaporation of the appropriate fractions in vacuo, affords 6-(triphenylmethylamino)-2,2-dimethyl-3-(1-furfuryltetrazol-5-yl)penam. The NMR spectrum of the product (CDCl$_3$) shows absorptions at 7.40 ppm m, 16H), 6.40 ppm (m, 2H), 5.50 ppm (s, 2H), 5.20 ppm (s, 1H), 4.90 ppm (m, 2H), 1.60 ppm (s, 3H), and 0.80 ppm (s, 3H).

PREPARATION D

6-(Triphenylmethylamino)-2,2-dimethyl-3-(1-[5-methylfurfuryl]tetrazol-5-yl)penam The title compound is prepared according to the procedure of Preparation C, but using 5-methylfurfurylamine in place of furfurylamine. The NMR spectrum (CDCl₃) of the product shows absorptions at 7.36 ppm (m, 15H), 6.33 ppm (m, 1H), 5.93 ppm (m, 1H), 5.50 ppm (s, 2H), 5.20 ppm (s, 1H), 4.50 ppm (m, 2H), 3.23 ppm d, 1H), 2.26 ppm (s, 3H), 1.63 ppm (s, 3H) and 0.90 ppm (m, 3H).

PREPARATION E

6-(Triphenylmethylamino)-2,2-dimethyl-3-(1-[2,4-dimethoxybenzyl]tetrazol-5-yl)penam The title compound is prepared in 46% overall yield from 6-(triphenylmethylamino)penicillanic acid, by replacing the furfurylamine of Preparation C with 2,4-dimethoxybenzylamine. The crude product is purified by recrystallization from a mixture of methylene chloride and methanol. The NMR spectrum of the product (CDCl₃) shows absorptions at 7.40 ppm (m, 16H), 6.45 ppm (m, 2H), 5.40 ppm (s, 2H), 4.50 ppm (m, 2H), 3.75 ppm (s, 3H), 3.70 ppm (s, 3H), 1.55 ppm (s, 3H) and 0.90 (s, 3H).

PREPARATION F

The procedure of Preparation E is repeated, except that the furfurylamine is replaced by an equimolar amount of the appropriate amine, to produce the following congeners:

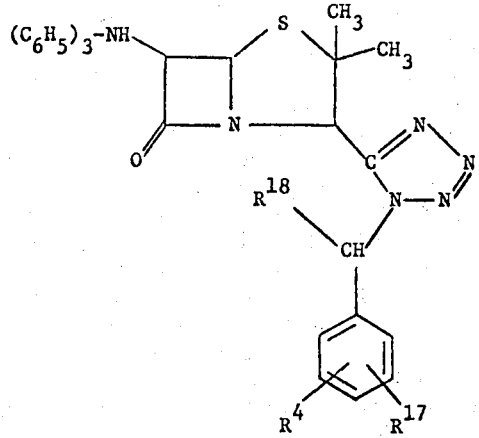

| R⁴ | R¹⁷ | R¹⁸ |
|---|---|---|
| 4-CH₃CH₂O | H | H |
| 3-Cl | 4-CH₃O | H |
| 3-CH₃ | 4-CH₃O | H |
| 3-C₆H₅ | 4-CH₃O | H |
| 4-CH₃O | H | CH₃ |
| H | H | C₆H₅ |
| 3-Br | H | C₆H₅ |
| 4-F | H | C₆H₅ |
| H | H | H |
| 4-C₆H₅ | H | H |
| H | H | CH₃ |
| 4-CH₃ | H | C₆H₅ |
| 4-n-C₃H₇O | H | H |
| H | 4-i-C₃H₇O | H |
| 2-CH₃O | 4-CH₃O | H |

PREPARATION G

6-(Triphenylmethylamino)-2,2-dimethyl-3-(1-[4-hydroxybenzyl]tetrazol-5-yl)penam A. 6-(Triphenylmethylamino)-2,2-dimethyl-3-(N-[4-hydroxybenzyl]carbamoyl)penam To a stirred slurry of 43.2 g. (0.20 mole) of 6-aminopenicillanic acid in 300 ml. of chloroform is added 55.6 ml. (0.40 mole) of triethylamine, followed by 61.2 g. (0.22 mole) of triphenylmethyl chloride, at ambient temperature. Stirring is then continued for a further 48 hours at ambient temperature.

A 120-ml. portion (containing 0.060 mole of triethylammonium 6-[triphenylmethylamino]penicillanate) of the above chloroform solution is withdrawn. It is diluted with a further 40 ml. of chloroform, and then 1.67 ml. (0.012 mole) of triethylamine is added. The mixture is cooled to ca. 4° C., in an ice-bath, and then 6.84 ml. of ethyl chloroformate is added all at once, with stirring. Stirring is continued for 30 minutes with ice-bath cooling, and then 7.5 g. (0.060 mole) of 4-hydroxybenzylamine is added. Stirring is continued for 10 minutes with ice-bath cooling, and then for a further 1 hour without cooling. At this point, the chloroform solution is washed with water, followed by brine, and then dried using anhydrous sodium sulfate. Removal of the solvent by evaporation in vacuo affords the crude amide. The crude amide is re-dissolved in 50 ml. of chloroform and absorbed on a column of chromatographic grade silica gel. The column is eluted with chloroform, taking 400 ml. fractions. Fractions 9 to 15 are combined and concentrated to an oil, which solidifies on trituration with methylene chloride. After further trituration with ether, there is obtained 12.63 g. of 6-(triphenylmethylamino)-2,2-dimethyl-3-(N-[4-hydroxybenzyl]carbamoyl)penam, m.p. 166°–168° C. (dec.). The infrared spectrum of the product (CHCl₃ solution) shows absorptions at 1785 cm⁻¹ (β-lactam) and 1675 cm⁻¹ (amide I). The NMR spectrum of the product (CDCl₃) shows absorptions at 7.60–6.40 ppm (multiplet, 20H, aromatic hydrogens and amide hydrogen), 4.70–4.10 ppm (multiplet, 5H, C-5 and C-6 hydrogens, benzyl methylene hydrogens and C-3 hydrogen), 2.98 ppm (doublet, 1H, amine nitrogen), 1.64 ppm (singlet, 3H, C-2 methyl hydrogens) and 1.31 ppm (singlet, 3H, C-2 methyl hydrogens).

B. 6-(Triphenylmethylamino)-2,2-dimethyl-3-(1-[4-hydroxybenzyl]tetrazol-5-yl)penam To a stirred solution of 1.69 g. (3 mmole) of 6-(triphenylmethylamino)-2,2-dimethyl-3-(N-[4-hydroxybenzyl]carbamoyl)penam (prepared as described in A) in 9 ml. of chloroform is added 1 ml. (12 mmole) of pyridine. The solution is cooled to ca. 4° C. in an ice-bath and 0.80 ml. of chlorotrimethylsilane is added. The solution is stirred for 40 minutes at ambient temperature, and then it is again cooled to ca. 4° C. Phosgene (1.5 ml. of a 4.3M solution in chloroform (6.45 mmole) is added and the cooling bath is removed. Stirring is continued for a further 1.5 hours, and then all the volatile components are removed by evaporation in vacuo.

The oily residue is redissolved in 6 ml. of chloroform and the solution is cooled to ca. 4° C. in an ice-bath. To the stirred solution is added 0.95 g. (6 mmole) of tetramethylguanidinium azide, and then stirring is continued for a further 1 hour at ambient temperature. At this point, 25 ml. of water is added, followed by sufficient 1 N sodium hydroxide to bring the pH of the aqueous phase to 10. The chloroform layer is separated off, washed with water, dried using sodium sulfate, and evaporated to dryness in vacuo. The oily residue (2.3 g.) is dissolved in a small volume of chloroform and absorbed on a column of 30 g. of chromatographic silica gel. The column is eluted with chloroform, taking 50-ml. fractions. Fractions 13 to 19 are combined and concentrated in vacuo to give 0.71 g. of 6-(triphenylmethylamino)-2,2-dimethyl-3-(1-[4-hydroxybenzyl]-tetrazol-5-yl)penam. The infrared spectrum of the product (in $CHCl_3$) shows an absorption at 1780 $cm^{-1}$ ($\beta$-lactam). The NMR spectrum ($CDCl_3$) shows absorptions at 7.80–6.67 ppm (multiplet, 20H, aromatic hydrogens and phenolic hydrogen), 5.66–5.10 ppm (quartet, 2H, benzyl methylene hydrogens), 5.02 ppm (singlet, 1H, C-3 hydrogen), 4.60–4.20 ppm (multiplet, 2H, C-5 and C-6 hydrogen), 3.10 ppm (doublet, 1H, amine hydrogen), 1.44 ppm (singlet, 3H, C-2 methyl hydrogens) and 0.71 ppm (singlet, 3H, C-2 methyl hydrogens).

PREPARATION H 6-(Triphenylmethylamino)-2,2-dimethyl-3-(1-[4-acetoxybenzyl]tetrazol-5-yl)penam To a stirred solution of 1.69 g. (3 mmole) of 6-(triphenylmethylamino)-2,2-dimethyl-3-(N-[4-hydroxybenzyl]carbamoyl)penam in 9 ml. of chloroform is added 1 ml. (12 mmole) of pyridine. The solution is cooled to ca. 4° C. in an ice-bath and 235 mg. of acetyl chloride is added slowly. The solution is stirred for 2 hours at ambient temperature, and then it is again cooled to ca. 4° C. Phosgene (1.5 ml. of a 4.3 M solution in chloroform [6.45 mmole]) is added and the cooling bath is removed. Stirring is continued for a further 1.5 hours, and then all the volatile components are removed by evaporation in vacuo. The residue is redissolved in 6 ml. of chloroform and the solution is cooled to ca. 4° C. in an ice-bath. To the stirred solution is added 0.95 g. (6 mmole) of tetramethylguanidinium azide, and then stirring is continued for a further 1 hour at ambient temperature. At this point, 25 ml. of water is added, followed by sufficient 1N sodium hydroxide to bring the pH of the aqueous phase to 10. The chloroform layer is separated off, washed with water, dried using sodium sulfate, and evaporated to dryness in vacuo. This affords crude 6-(triphenylmethylamino)-2,2-dimethyl-3-(1-[4-acetoxybenzyl]tetrazol-5-yl)penam, which is purified further by chromatography.

When the above procedure is repeated, except that the acetyl chloride is replaced by an equimolar amount of formic-acetic anhydride and chloromethyl methyl ether, respectively, the product is 6-(triphenylmethylamino)-2,2-dimethyl-3-(1-[4-formyloxybenzyl]tetrazol-5-yl)penam and 6-(triphenylmethylamino)-2,2-dimethyl-3-(1-[4-methoxymethoxy)benzyl]tetrazol-5-yl)penam, respectively.

PREPARATION I

6-Amino-2,2-dimethyl-3-(1-[4-methoxybenzyl]tetrazol-5-yl)penam p-toluenesulfonate To a stirred slurry of 143 g. of 6-(triphenylmethylamino)-2,2-dimethyl-3-(1-[4-methoxybenzyl]tetrazol-5-yl)penam in 1,000 ml. of dry acetone is added 45.0 g. of p-toluenesulfonic acid monohydrate, at ambient temperature. The solids slowly dissolve, giving a clear solution. After about 15 minutes, the product starts to precipitate. Stirring is continued for a further 45 minutes after the product starts to appear, and then a first crop of product is filtered off and washed with chloroform. The acetone is evaporated to dryness, and the solid residue is slurried for 45 minutes in 300 ml. of chloroform. This affords a second crop of product. The two crops are combined, slurried for 1 hour in 1,000 ml. of chloroform, filtered off, and dried in vacuo giving 123 g. of 6-amino-2,2-dimethyl-3-(1-[4-methoxybenzyl]tetrazol-5-yl)penam p-toluenesulfonate, m.p. 174°–175.5° C. The infrared spectrum (KBr disc) of the product shows an absorption band at 1795 $cm^{-1}$. The NMR spectrum (in DMSO-$d_6$) shows absorption bands at 7.20 ppm (multiplet, aromatic hydrogens), 5.80 ppm (multiplet, benzyl hydrogens, C-5 hydrogen and C-3 hydrogens), 5.20 ppm (doublet, C-6 hydrogen), 3.75 ppm (singlet, methoxy hydrogens, 2.35 ppm (singlet, sulfonate methyl hydrogens), 1.70 ppm (singlet, C-2 methyl hydrogens) and 0.85 ppm (singlet, C-2 methyl hydrogens).

PREPARATION J

Reaction of the appropriate 6-(triphenylmethylamino)-2,2dimethyl-3-(1-substituted tetrazol-5-yl)penam with p-toluenesulfonic acid monohydrate, substantially according to the procedure of Preparation I provides the following compounds as their p-toluenesulfonate salts:

| Compound | Yield |
| --- | --- |
| 6-amino-2,2-dimethyl-3-(1-[4-benzyloxybenzyl]tetrazol-5-yl)-penam | 79 |
| 6-amino-2,2-dimethyl-3-(1-furfuryltetrazol-5-yl)penam | 62 |
| 6-amino-2,2-dimethyl-3-(1-[5-methylfurfuryl]tetrazol-5-yl)penam | 54 |
| 6-amino-2,2-dimethyl-3-(1-[2,4-dimethoxybenzyl]tetrazol-5-yl)penam | 99 |

To a stirred solution of 304 mg. of 6-amino-2,2-dimethyl-3-(1-[4-benzyloxybenzyl]tetrazol-5-yl)penam p-toluenesulfonate in 10 ml. of methylene chloride is added 69.7 $\mu$l of triethylamine. After 3 minutes, 5 ml. of water are added and the mixture is stirred vigorously. The organic phase is then removed, diluted with ether, dried using anhydrous magnesium sulfate, and evaporated to dryness in vacuo. The residue is 189 mg. (86% yield) of 6-amino-2,2-dimethyl-3-(1-[4-benzyloxybenzyl]-tetrazol-5-yl)penam free base.

In like manner the products of Preparations F-H and S-U are detritylated to the corresponding 6-amino derivatives.

PREPARATION K

6-Amino-2,2-dimethyl-3-(5-tetrazolyl)penam

A stirred solution of 32.0 g. of 6-amino-2,2-dimethyl-3-(1-[4-methoxybenzyl]tetrazol-5-yl)penam p-toluenesulfonate, and 24 ml. of anisole, in 96 ml. of trifluoroacetic acid is maintained at 40 ± 1° C. for 35 minutes. The trifluoroacetic acid is then removed rapidly by vacuum distillation. A 120-ml portion of ether is added to the residue, which produces a white flocculent suspension. The suspension and solvent is cooled to about 0° C., and to it is then added, portionwise, 80 ml. of 2N sodium hydroxide, giving two clear phases. The pH of the aqueous phase at this point is about 2.7 The layers are separated, and the ether phase is discarded. The pH of the aqueous phase is raised to 4.1 with 2N sodium hydroxide. This aqueous phase is then washed with 100 ml. of ether and filtered. It is combined with the corresponding aqueous phases from four other identical experiments, and the total aqueous soluton is lyophilized to give crude 6-amino-2,2-dimethyl-3-(5-tetrazolyl)penam. This crude product is slurried in a small amount of water and filtered off. It is then resuspended in water and brought into solution by raising the pH to 7.4 by the addition of sodium hydroxide solution. The clear solution is extracted with ether and the extracts are discarded. The pH of the aqueous phase is adjusted to 4.1 using dilute hydrochloric acid, and the product which precipitates is filtered off. The infrared spectrum of the product shows an absorption at 1795 cm$^{-1}$. Its NMR spectrum (in DMSO-d$_6$) shows absorptions at 5.65 ppm (doublt C-5 hydrogen), 5.20 ppm (singlet, C-3 hydrogen), 4.70 ppm (doublet, C-6 hydrogen), 1.65 ppm (singlet, C-2 methyl hydrogens) and 1.10 ppm (singlet, C-2 methyl hydrogens).

When each of the 6-amino-2,2-dimethyl-3-(1-substituted tetrazol-5-yl) penam p-toluenesulfonate salts of Preparation J is treated with trifluoroacetic acid-/anisole, according to the above procedure, the product in each case is 6-amino-2,2-dimethyl-3-(5-tetrazolyl)penam.

PREPARATION L 6-(Triphenylmethylamino)-2,2-dimethyl-3-(5-tetrazolyl)penam

To a stirred solution of 1.69 g. (3 m mole) of 6-triphenylmethylamino)-2,2-dimethyl-3-(N-[4-hydroxybenzyl]penam prepared as described in (Preparation G) in 9 ml. of chloroform is added 1 ml. (12 mmole) of pyridine. The solution is cooled to ca. 4° C. in an ice-bath and 0.80 ml. of chlorotrimethylsilane is added. The solution is stirred for 40 minutes at ambient temperature, and then it is again cooled to ca. 4° C. Phosgene (1.5 ml. of a 4.3 M solution in chloroform 6.45 mmole) is added and the cooling bath is removed. Stirring is continued for a further 1.5 hours, and then all the volatile components are removed by evaporation in vacuo. The oily residue is redissolved in 6 ml. of chloroform and the solution is cooled to ca. 4° C. in an ice-bath. To the stirred solution is added 0.95 g. (6 mmole) of tetramethylguanidinium azide, and then stirring is continued for a further 1 hour at ambient temperature. At this point, 25 ml. of water is added, followed by sufficient 1N sodium hydroxide to bring the pH of the aqueous phase to 10. The chloroform layer is removed, washed with water, dried using sodium sulfate, and evaporated to dryness in vacuo. This affords crude 6-(triphenylmethylamino)-2,2-dimethyl-3-(1-[4-trimethylsilyloxybenzyl]tetrazol-5-yl)penam, which is purified by chromatography on silica gel using chloroform as eluant.

To a stirred solution of 200 mg. of the purified trimethylsilyloxybenzyl derivative, in 4 ml. of tetrahydrofuran, is added 0.3 ml. of 1.0N sodium hydroxide. The solution is stirred at ambient temperature for 50 minutes, and then the pH is adjusted to 5.7 using 5% hydrochloric acid. The solvent is removed by evaporation in vacuo to yield crude 6-(triphenylmethylamino)-2,2-dimethyl-3-(5-tetrazolyl)penam.

PREPARATION M 6-(Triphenylmethylamino)-2,2-dimethyl-3-(1-[ethoxycarbonyl]tetrazol-5-yl)penam A. 6-(Triphenylmethylamino)-2,2-dimethyl-3-(N-ethoxycarbonylcarbamoyl)penam.

To a stirred solution of 4.58 g. (10 mmole) 6-triphenylmethylamino)penicillanic acid and 1.45 ml. (10 mmole) of triethylamine, in 75 ml. of acetonitrile, is added 1.15 g. (10 mmole) of ethoxycarbonyl isocyanate dissolved in 5 ml. of acetonitrile. The resulting solution is stirred at ca. 25° C. for 16 hours, and then the solvent is removed by evaporation in vacuo. The residue is re-dissolved in chloroform, and the chloroform solution is washed successively with water, sodium bicarbonate solution and sodium chloride solution. The chloroform solution is then dried using anhydrous magnesium sulfate, and evaporated in vacuo. The residue is again re-dissolved in chloroform, and the chloroform solution is washed with dilute hydrochloric acid, dried using magnesium sulfate, and again evaporated in vacuo. This affords the crude product, which is purified by chromatography using silica gel as the adsorbant and eluting the column with chloroform containing 4% by volume of ethanol. The final yield of 6-(triphenylmethylamino)-2,2-dimethyl-3-(N-[ethoxycarbonyl]carbamoyl)-penam is 2.54 g. (48% yield).

B. 6-(Triphenylmethylamino)-2,2-dimethyl-3-(1-[ethoxycarbonyl]tetrazol-5-yl)penam To a stirred solution of 529 mg. (1 mmole) of 6-(triphenylmethylamino)-2,2-dimethyl-3-(N-[ethoxycarbonyl]carbamoyl)penam and 240 mg. (3 mmole) of pyridine, in 25 ml. of methylene chloride, is added 208 mg. (1 mmole) of phosphorus pentachloride, at 0° C. The reaction mixture is stirred at 0° C. for 0.5 hour and then at ca. 25° C. for 2 hours. The solvents and the excess pyridine are then removed by evaporation in vacuo, and the residue is re-dissolved in 15 ml. of chloroform. The latter chloroform solution is cooled to 0° C., and 0.47 g. (3 mmole) of tetramethylguanidinium azide is added in several small portions with stirring. Stirring is continued for 2 hours at ambient temperature, and then to the reaction mixture is added a further 15 ml. of chloroform followed by 30 ml. of water. The pH is adjusted to 6.5, and then the chloroform layer is removed. The chloroform solution is washed with water followed by brine, and then it is dried using anhydrous sodium sulfate. Removal of the solvent by evaporation in vacuo affords crude 6-(triphenylmethylamino)-2,2-dimethyl-3-(1-[ethoxycarbonyl]tetrazol-5-yl)penam. The crude product is purified further by chromatography using silica gel.

PREPARATION N

Starting with 6-(triphenylmethylamino)penicillanic acid and the appropriate isocyanate, and following the procedure of Preparation M, the following compounds are prepared:

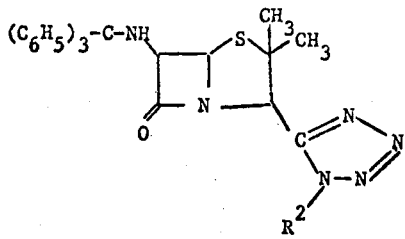

| R² |
|---|
| C₆H₅CH₂O—CO— |
| C₆H₅O—CO— |
| (4-NO₂—C₆H₄)O—CO— |
| (3,4-Cl₂—C₆H₃)O—CO— |
| CH₃—SO₂— |
| C₆H₅CH₂—SO₂— |
| C₆H₅—SO₂— |
| (3-CH₃O—C₆H₄)—SO₂— |
| (2,4-[NO₂]₂—C₆H₃)—SO₂ |

PREPARATION O 6-(Triphenylmethylamino)-2,2-dimethyl-3-(5-tetrazolyl)penam

To a stirred mixture of 2 ml. of tetrahydrofuran and 4 ml. of water is added 150 mg. of 6-(triphenylmethylamino)-2,2-dimethyl-3-(1-[ethoxycarbonyl]tetrazol-5-yl)penam. The pH of the mixture is adjusted to 9.5, and stirring is continued at that pH for a further 30 minutes, at ambient temperature. The bulk of the tetrahydrofuran is removed by evaporation in vacuo, and the residue is partitioned between water and ethyl acetate at pH 9. The ethyl acetate is removed and discarded. Fresh ethyl acetate is added and the pH is adjusted to 2.0. The ethyl acetate layer is removed, washed with water, dried using anhydrous sodium sulfate, and evaporated in vacuo to give the crude title compound.

When each of 6-(triphenylmethylamino)-2,2-dimethyl-3-(1-substituted tetrazol-5-yl)penam compounds of Preparation N is hydrolyzed using the above procedure, the product in each case is also 6-(triphenylmethylamino)-2,2-dimethyl-3-(5-tetrazolyl)penam.

PREPARATION P

6-Amino-2,2-dimethyl-3-(5-tetrazolyl)penam

To a slurry of dry acetone (5 ml.) and 6-triphenylmethylamino-2,2-dimethyl-3-(5-tetrazolyl)penam (483 mg., 1.0 mmole) at room temperature is added p-toluenesulfonic acid monohydrate (209 mg., 1.1 mmole). The resulting solution is stirred for 10 minutes and then ether (30 ml.) is added over a 5 minute period. The mixture is stirred for 10 minutes after which the solvent is decanted from the solid which separates. The solid is dissolved in tetrahydrofuran (30 ml.) and placed on a column (300 × 6 mm.) packed with 10 g. of Florisil (synthetic magnesium silicate). The column is washed with tetrahydrofuran until a total of 125 ml. is collected. The eluate is concentrated to dryness under reduced pressure at 40° C. to give 210 mg. of solid. The solid is slurried in ether (30 ml.), filtered, washed with ether and air-dried. Yield = 121 mg. (50%). The NMR spectrum (in DMSO-d₆) shows absorption bands at 1.08 ppm, (2s, 3H each, C-2 methyls), 4.60 + 5.52 (2d, J=4.0 H_z, 2H, H₅ + H₆), 5.10 (s, 1H H₃) and 5.88 (s, 3H, NH₃)ppm. (s, 3H), 1.59ppm (s,3H), 4.60 ppm (d,1H), 5.52 ppm (d,1H), 5.10ppm (s, 1H), and 5.88 ppm (s,3H).

PREPARATION Q

6-Amino-2,2-dimethyl-3-(1-[ethoxycarbonyl]tetrazol-5-yl)penam

To a stirred solution of 554 mg. of 6-(triphenylmethylamino)-2,2-dimethyl-3-(1-[ethoxycarbonyl]tetrazol-5-yl)penam in 2 ml. of acetone is added a solution of 190 mg. of p-toluenesulfonic acid monohydrate in 1 ml. of acetone. Stirring is continued for a further 3 hours, and then the acetone is removed by evaporation in vacuo. The residue is slurried in ether, filtered and dried, to give the title compound as its p-toluenesulfonate salt.

The above p-toluenesulfonate salt is added to a mixture of 15 ml. of water and 15 ml. of chloroform. The pH of the aqueous phase is adjusted to 7.0 and the chloroform layer is removed. The chloroform is dried using sodium sulfate, and then it is evaporated in vacuo to give the title compound as its free base.

PREPARATION R

Reaction of the appropriate 6-(triphenylmethylamino)-2,2-dimethyl-3-(1-substituted tetrazol-5-yl)penam chosen from those in Preparation N with p-toluenesulfonic acid, according to the procedure of Preparation Q provides the following compounds as their p-toluenesulfonate salts.

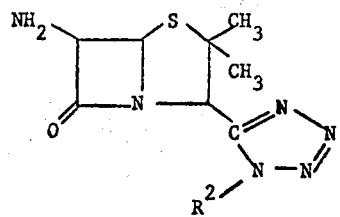

| R² |
|---|
| C₆H₅CH₂O—CO— |
| C₆H₅O—CO— |
| (4-NO₂—C₆H₄)O—CO— |
| (3,4-Cl₂—C₆H₃)O—CO |
| CH₃—SO₂— |
| C₆H₅CH₂—SO₂— |
| C₆H₅—SO₂— |
| (3-CH₃O—C₆H₄)—SO₂)— |
| (2,4-[NO₂]₂—C₆H₃)—SO₂ |

PREPARATION S 6-(Triphenylmethylamino)-2,2-dimethyl-3-(1-[2-methoxycarbonylethyl]tetrazole-5-yl)penam A. 6-(Triphenylmethylamino)-2,2-dimethyl-3-(N-[2-methoxycarbonylethyl]carbamoyl)penam To a stirred solution of 35 g. of 6-(triphenylmethylamino)penicillanic acid in 250 ml. of dry, ethanol-free chloroform, is added 11.7 ml. of triethylamine at 0°–3° C. The solution thus obtained is then added dropwise, with stirring, at 0°–6° C., to a second solution, prepared from 7.3 ml. of ethyl chloroformate in 155 ml. of dry, ethanol-free chloroform. Stirring is continued for a further 10 minutes. This affords a chloroform solution of the mixed anhydride of 6-(triphenylmethylamino)penicillanic acid.

In a separate flask, a solution of β-alanine methyl ester is prepared by adding 11.7 ml. of triethylamine to a slurry of 10.73 g. of β-alanine methyl ester hydrochloride and 2 g. of anhydrous sodium sulfate in 115 ml. of dry, ethanol-free chloroform, at ca. 10° C. Stirring is continued for a further 10 minutes.

The latter amino-ester solution is then added dropwise, with stirring at 3°–6° C., to the above-described mixed anhydride solution. After the end of the addition, stirring is continued for a further 2 hours.

At this point, the reaction solution is washed successively with three portions of water and one portion of brine. The solution is then dried using anhydrous sodium sulfate, and evaporated in vacuo to give 40.1 g. of crude 6-(triphenylmethylamino)-2,2-dimethyl-3-(N-[2-methoxycarbonylethyl]carbamoyl)penam as a glassy solid, m.p. 60°–70° C. The crude product is purified by extracting it into refluxing ether, treating the filtered solution with activated carbon, and then re-precipitating the product by the addition of petroleum ether.

B. 6-(triphenylmethylamino)-2,2-dimethyl-3-(1-[2-methoxycarbonylethyl]tetrazol-5-yl)penam To a stirred solution of 2 g. of the amide described under A above, in 5 ml. of dry, ethanol-free chloroform, is added, at ca. 0° C., 1.36 ml. of pyridine, followed by a solution of 620 mg. of phosgene in 4 ml. of dry, ethanol-free chloroform. The solution is stirred for 2.5 hours, at ambient temperature, and then the solvent is removed by evaporation in vacuo. The residue is re-dissolved in 9 ml. of dry, ethanol-free chloroform, and 580 mg. of tetramethylguanidinium azide is added. The reaction mixture is stirred for 45 minutes, at which point a further 200 mg. of tetramethylguanidinium azide is added. The reaction mixture is then stirred 18 hours to complete the conversion to tetrazole. To the reaction solution is then added saturated sodium bicarbonate solution, in sufficient quantity that the pH of the aqueous phase is 7.6. The chloroform layer is removed, washed with water at pH 5, washed with water at pH 7, dried using anhydrous sodium sulfate, and finally evaporated in vacuo. This affords 2.19 g. of crude product, which is recrystallized from methanol giving 1.11 g (48% yield) of product with m.p 100°–105° C. The NMR spectrum (CDCl$_3$) shows absorptions at 7.40 ppm (m, 15H), 5.15 ppm (s, 1H), 3.80 (m, 4H), 3.70 ppm (s, 3H), 3.10 ppm (t, 2H), 1.70 ppm (s, 3H) and 1.17 ppm (s, 3H), and further indicates that the product contains methanol of solvation.

PREPARATION T

The procedure of Preparation S is repeated except that the β-alanine methyl ester is replaced by the appropriate amine to produce the following compounds

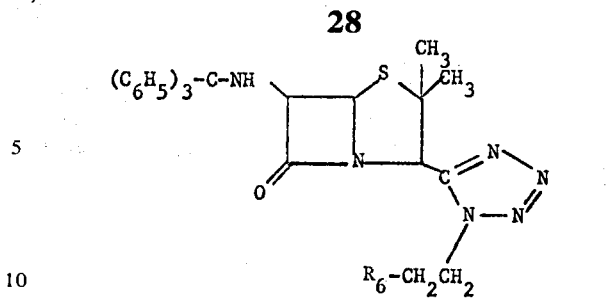

| R$_6$ |
|---|
| CN |
| C(=O)—O—CH(CH$_3$)$_3$ |
| C(=O)—O—C$_6$H$_5$ |
| SO$_2$—CH$_3$ |
| SO$_2$—C$_6$H$_5$ |
| SO$_2$—N(CH$_3$)$_2$ |
| SO$_2$—N(C$_6$H$_5$)$_2$ |
| SO$_2$—NH—CH$_2$—C$_6$H$_5$ |

PREPARATION U 6-(Triphenylmethylamino)-2,2-dimethyl-3-(5-tetrazolyl)penam

To a stirred solution of 600 mg. of 6-(triphenylmethylamino)-2,2-dimethyl-3-(1-[2-methoxycarbonylethyl]tetrazol-5-yl)penam (containing ca 4.5% of methanol) in 1 ml. of chloroform, is added a solution of 375.2 mg. of diazabicyclo[4.3.0]non-5-ene in 0.5 ml. of chloroform. Stirring is continued for a further 3 hours, and then the solution is diluted with a further 2 ml. of chloroform. The latter solution is washed quickly with 5 ml. of 2N hydrochloric acid, and then a further 5 ml. of 2N hydrochloric are added. The resulting mixture is cooled to ca 0° C., and the solid which precipitates is filtered off, giving 323 mg. (71% yield) of the title compound. The NMR spectrum (DMSO-d$_6$) of the product shows absorptions at 7.40 ppm (m, 15H), 5.30 ppm (s, 1H), 4.60 ppm (m, 2H), 1.58 ppm (s, 3H) and 0.78 ppm (s, 3H).

Reaction of each of the 6-(triphenylmethylamino)-2,2-dimethyl-3-(1-substituted tetrazol-5-yl)penam compounds of Preparation S with diazobicyclo (4.3.9) non-5-ene, according to the above procedure, produces in each case, 6-(triphenylmethyl amino)-2,2-dimethyl-3-(tetrazol-5-yl)penam.

PREPARATION V

6-Amino-2,2-dimethyl-3-(2-[pivaloyloxymethyl]tetrazol-5-yl)penam

To a stirred solution of 0.932 g. (7.21 m mole) of quinoline in 8.0 ml. of chloroform is added 0.840 g. (4.05 m mole) of phosphorus pentachloride. The suspension is cooled to −15° C., and then 1.81 g. (3.84 m mole) of 6-(2-phenylacetamido)-2,2-dimethyl-3-(2-[pivaloyloxymethyl]tetrazol-5-yl)penam is added. Stirring is continued for a further 30 minutes, at ca.−5° C., and then 2.15 g. (35.7 m mole) of n-propanol is added. Stirring is continued for a further 30 minutes, again at ca. −5° C., and then 25 ml. of 90:10 isopropyl ether-acetone is added, followed immediately by a solution of 1.35 g. of sodium chloride in 6.02 ml. of water. The temperature rises to 15° C. and then it is lowered again to −15° C. The precipitate which has formed is filtered off and dried, giving 1.33 g. (88% yield) of 6-amino-2,2-dimethyl-3-(2-[pivaloyloxymethyl]tetrazol-5-yl)penam hydrochloride. The infrared spectrum (KBr disc) shows absorptions at 1785 cm⁻¹ (β-lactam) and 1750 cm⁻¹ (ester). The NMR spectrum (DMSO-d₆) shows absorptions at 6.70 ppm (singlet, 2H, pivaloyloxy methylene hydrogens), 5.75 ppm (doublet, 1H, C-5 hydrogen), 5.50 ppm (singlet, 1H, C-3 hydrogen), 5.70 ppm (doublet, 1H, C-6 hydrogen), 1.75 ppm (singlet, 3H, C-2 methyl hydrogens), 1.20 ppm (singlet, 9H, t-butyl hydrogens) and 1.10 ppm (singlet, 3H, C-2 methyl hydrogens).

PREPARATION W

6-Amino-2,2-dimethyl-3-(1-[pivaloyloxymethyl]tetrazol-5-yl)penam

The title compound is prepared as its hydrochloride in 90% yield, from 6-(2-phenylacetamido)-2,2-dimethyl-3-(1-[pivaloyloxymethyl]-tetrazol-5-yl)penam, using the method of Preparation V. The infrared spectrum (KBr disc) shows absorptions at 1780 cm⁻¹ (β-lactam) and 1740 cm⁻¹ (ester). The NMR spectrum (DMSO-d₆) shows absorptions at 6.71 ppm (singlet, 2H, pivaloyloxy methylene hydrogens), 5.88 ppm (singlet, 1H, C-3 hydrogen), 5.83 ppm (doublet, 1H, C-5 hydrogen), 5.20 ppm (doublet, 1H, C-6 hydrogen), 1.80 ppm (singlet, 3H, C-2 methyl hydrogens), 1.20 ppm (singlet, 9H, t-butyl hydrogens) and 1.16 ppm (singlet, 3H, C-2 methyl hydrogens).

PREPARATION X

6-Amino-2,2-dimethyl-3-(1-pivaloyloxymethyltetrazol-5-yl)penam and
6-Amino-2,2-dimethyl-3-(2-pivaloyloxymethyltetrazol-5-yl)penam To a stirred suspension of 2.40 g. of 6-amino-2,2-dimethyl-3(5-tetrazolyl)penam in 15 ml. of N,N-dimethylformamide, is added 2.8 ml. of triethylamine. Stirring is continued for a further 15 minutes, and then 2.68 g. of chloromethyl pivalate is added. The mixture is stirred at ambient temperature for 5 hours, and then it is diluted with 100 ml. of water. It is then extracted with ethyl acetate. The extract is washed with water, dried using anhydrous sodium sulfate, and then it is evaporated in vacuo to give a mixture of the title compounds. The individual isomers are obtained by chromatographic separation of the crude product.

Repetition of this procedure but substituting 3-bromophthalide or the appropriate alkanoyloxyalkyl chloride for pivaloyloxymethyl chloride affords an isomeric mixture of the corresponding monoalkylated products in which the alkanoyloxyalkyl or phthalidyl substituent is located at the 1- or the 2-position of the tetrazole ring. The following compounds are thus prepared. (For convenience only the alkyl substituent is tabulated):

acetoxymethyl
isobutyryloxymethyl
hexanoyloxymethyl
1-acetoxyethyl
1-pivaloyloxyethyl
1-hexanoyloxyethyl
phthalidyl
propionyloxymethyl

PREPARATION Y

6-Amino-2,2-dimethyl-3-(1[2]-triphenylmethyltetrazol-5-yl)penam

To a stirred slurry of 240 mg. of 6-amino-2,2-dimethyl-3-(5-tetrazolyl)penam in 1.5 ml. of dry, ethanol-free chloroform, is added 0.36 ml. of triethylamine. The mixture is stirred until a cloudy isolution is obtained, and then ca. 200 mg. of anhydrous sodium sulfate is added. Stirring is continued for a further 15 minutes and then the mixture is filtered. To the filtrate is added 278.5 mg. of triphenylmethyl chloride, and the reaction mixture is stored at ambient temperature for 4.5 hours. At this point, the solvent is removed by evaporation in vacuo, leaving the crude title product as a mixture of isomers as indicated. The crude product is re-dissolved in a small volume of chloroform and then adsorbed on a small column of silica gel. The column is eluted with chloroform and the first 20 ml. of eluate are collected and evaporated to dryness in vacuo. A small volume of ether is added to the residue, and the mixture is again evaporated to dryness in vacuo. The latter residue is washed with ether, to give 357.4 mg. (77% yield) of a white solid. The NMR spectrum (CDCl₃) shows absorptions at 7.15 ppm (broad singlet), 5.70 ppm (doublet), 5.35 (singlet), 4.55 (doublet), 1.60 (singlet) and 1.10 (singlet).

PREPARATION Z

Reaction of 6-amino-2,2-dimethyl-3-(5-tetrazolyl)penam with a substituted triphenylmethyl chloride as alkylating agent according to the procedure of Preparation Y affords in each case a mixture of the corresponding 6-amino-2,2-dimethyl-3-(1-[substituted triphenylmethyl]tetrazol-5-yl)penam and 6-amino-2,2-dimethyl-3-(2-[substituted triphenylmethyl]tetrazol-5-yl)penam compounds. In this way, the mixtures of the following compound and its isomer are produced:

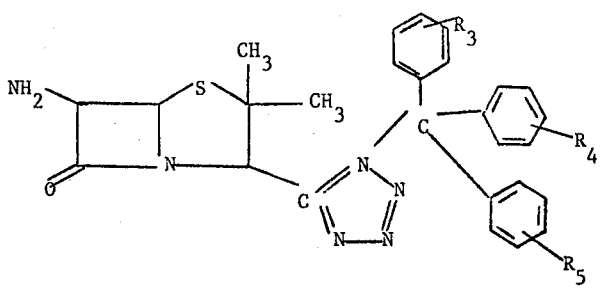

| $R_3$ | $R_4$ | $R_5$ |
|---|---|---|
| 2-F | H | H |
| 3-Cl | H | H |
| 4-Br | H | H |
| 2-$C_2H_5$ | H | H |
| 4-n-$C_3H_7$ | H | H |
| 3-sec-$C_4H_9$ | H | H |
| 4-$OC_2H_5$ | H | H |
| H | 4-$C_6H_5$ | H |
| H | 3-$CH_3$ | 3-$CH_3$ |
| H | 3-Cl | 3-Cl |
| 4-Cl | H | 4-$OCH_3$ |
| 4-$C_6H_5$ | H | 4-$C_6H_5$ |
| 4-$CH_3$ | 4-$CH_3$ | 4-$CH_3$ |
| 4-i-$C_3H_7$ | 3-$OCH_3$ | 3-$OCH_3$ |

The mixtures are separated into the two isomers by chromatography.

PREPARATION AA

Mono-Trimethylsilyl Derivative of 6-Amino-2,2-Dimethyl3-(5-Tetrazolyl)Penams

To a stirred suspension of 2.4 g. of 6-amino-2,2-dimethyl-3-(5-tetrazolyl)penam in 50 ml. of chloroform is added 2.8 ml. of triethylamine. Stirring is continued for a further 15 minutes, and then the solution thus obtained, is cooled to 0° C. To this solution is then added 1.08 g. of trimethylsilyl chloride. The cooling bath is removed, and the reaction mixture is stirred for a further one hour at ambient temperature, to give a chloroform solution of the mono-trimethylsilyl derivative of 6-amino-2,2-dimethyl-3-(5-tetrazolyl)penam.

When the above procedure is repeated, except that the trimethylsilyl chloride used therein is replaced by an equimolar amount of triethylsilyl chloride and tri-n-butylsilyl chloride, respectively, the products are the mono-triethylsilyl and the mono-tri-n-butylsilyl derivative of 6-amino-2,2-dimethyl-3-(5-tetrazolyl)penam, respectively.

PREPARATION BB

Bis-Trialkylsilyl Derivatives of 6-Amino-2,2-dimethyl-3-(5-Tetrazolyl)penam

To a stirred suspension of 2.4 g. of 6-amino-2,2-dimethyl-3-(5-tetrazolyl)penam in 50 ml. of chloroform is added 4.2 ml. of triethylamine. Stirring is continued for a further 15 minutes, and the solution thus obtained is cooled to 0° C. To this solution is then added 2.16g. of trimethylsilyl chloride. The cooling bath is removed, and the reaction mixture stirred at ambient temperature for 1 hour and then is refluxed for 1 hour. It is then cooled to ambient temperature giving a chloroform solution of the bistrimethylsilyl derivative of 6-amino-2,2-dimethyl-3-(5-tetrazolyl)penam.

When the above procedure is repeated, except that the trimethylsilyl chloride used therein is replaced by an equimolar amount of triethylsilyl chloride and triisopropylsilyl chloride, respectively, the products are the bis-triethylsilyl and the bis-triisopropyl derivative of 6-amino-2,2-dimethyl-3-(5-tetrazolyl)penam, respectively.

PREPARATION CC 6-(2-Phenylacetamido)-2,2-dimethyl-3(5-tetrazolyl)penam

A flask containing 965 mg. of 6-amino-2,2-dimethyl-3-(1-[4-methoxybenzyl]tetrazol-5-yl)penam p-toluenesulfonate, 40 drops of anisole, and 5 ml. of trifluoroacetic acid is immersed in a water-bath maintained at 35°–40° C. The progress of the reaction is followed by removing samples at intervals, and recording their nuclear magnetic resonance spectra. After about 25 minutes, the removal of the 4-methoxybenzyl group is found to be approximately 90% complete. At this point the reaction solution is added to a rapidly-stirred, ice-cold solution of 10 ml. of pyridine in 50 ml. of chloroform. Stirring is continued for 5 minutes, and then 0.24 ml of phenylacetyl chloride is added. The cooling bath is removed and the reaction mixture is stirred for a further 20 minutes. A 100-ml. portion of water is added, and the pH of the aqueous phase is then adjusted to 2.5 by the dropwise addition of 0.5 N hydrochloric acid. The chloroform layer is separated off, washed with saturated brine, dried using anhydrous sodium sulfate and then it is evaporated to dryness in vacuo. The crude product thus obtained is re-dissolved in chloroform, and the solution is divided into two equal portions. To one of these portions is added an equal volume of water. The layers are stirred vigorously and the pH of the aqueous phase is raised to 6.9 by the dropwise addition of 0.1N sodium hydroxide solution. The chloroform is separated off and discarded, and then an equal quantity of the fresh chloroform is added to the aqueous phase. The layers are stirred vigorously and the pH is adjusted to 2.5 using dilute hydrochloric acid. The chloroform is separated off, washed with saturated brine, dried using anhydrous magnesium sulfate and then evaporated to dryness in vacuo. This affords 197 mg. of an oily residue. The residue is re-dissolved in 3 ml. of chloroform which is then added dropwise to 30 ml. of hexane. The fluffy white solid which precipitates is filtered off, giving 80 mg. of 6-(2-phenylacetamido)-2,2-dimethyl-3-(5-tetrazolyl)penam. IR(KBr disc): 1795, 1660 and 1510 cm$^{-1}$. NMR ($DCDl_3$): 7.20 ppm (s,5H), 5.55 ppm (m,2H), 5.15 ppm (s, 1H), 3.60 ppm (s, 2H), 1.40 ppm (s, 3H) and 1.05 ppm (s, 3H).

The MIC of the title compound against a strain of *Streptococcus pyogenes* is <0.1 µg/ml.

PREPARATION DD 6-(2-Phenoxyacetamido)-2,2-dimethyl-3-(5-tetrazolyl)penam

A stirred slurry of 480 mg, of 6-amino-2,2-dimethyl-3-(5-tetrazolyl)penam in 10 ml. of water is cooled to 0° C., and then the pH is adjusted to 8.0 using 1N sodium hydroxide. To this solution is then added 0.25 ml. of phenoxyacetyl chloride, in portions, with the pH of the solution being maintained between 7 and 8 during the addition, using 0.1N sodium hydroxide. The solution is stirred for a further 30 minutes at 0° C. at pH 8. It is then extracted with chloroform, and the extracts are discarded. The aqueous phase is acidified to pH 2 with dilute hydrochloric acid, and then it is further extracted with chloroform. The latter extracts are dried using calcium sulfate and then evaporated in vacuo to give the crude product as a gummy solid. This is purified by dissolving it in 20 ml. of chloroform, and adding the resultant solution dropwise to 250 ml. of hexane. The precipitate which forms is filtered off, giving 385 mg. of 6-(2-phenoxyacetamido)-2,2-dimethyl-3-(5-tetrazolyl)penam as a white amorphous solid. IR spectrum (KBr disc): 1785, 1670 and 1540 cm$^{-1}$. NMR spectrum (DMSO-$d_6$): 7.50–6.70 ppm (m,5H), 5.70 ppm (m,2H), 5.35 ppm (s, 3H), 4.60 ppm (s, 2H), 1.60 ppm (s, 3H) and 1.05 ppm (s,3H).

The MIC of the title compound against a strain of *Streptococcus pyogenes* is <0.1 µg/ml.

In like manner the 6-amino-2,2-dimethyl-3-(substituted tetrazol-5-yl) penams of Preparations I, J. Q, R. V-Z, AA and BB are acylated with phenoxyacetyl chloride and phenylacetyl chloride to produce the corresponding acyl derivatives.

PREPARATION EE 6-(D-2-Amino-2-phenylacetamido)-2,2-dimethyl-3-(5-tetrazolyl) penam To a stirred solution of 23.8 ml. of ethyl chloroformate in 600 ml. of acetone, is added 25 ml. of a 3% solution of N-methylmorpholine in acetone. The resulting solution is cooled to −40° C., and then 75.2 g. of sodium N-(2-methoxycarbonyl-1-methylvinyl)-D-2-amino-2-phenylacetate is added. The temperature is adjusted to −20° C. and stirring is continued for 28 minutes. The solution is re-cooled to −40° C., and an ice-cold solution, prepared by suspending 60.0 g. of 6-amino-2,2-dimethyl-3-(5-tetrazolyl)penam in 250 ml. of water and then adjusting the pH to 7.0, is added. The resulting solution is stirred for 30 minutes without further cooling, and then the acetone is removed by evaporation in vacuo. To the aqueous residue is added an equal volume of tetrahydrofuran, and then, at 5° C. the pH is adjusted to 1.5 with dilute hydrochloric acid. The mixture is held at this temperature and pH for 30 minutes, and then the tetrahydrofuran is removed by evaporation in vacuo. The aqueous residue is extracted with ethyl acetate, followed by ether, and the extracts are discarded. The pH of the remaining aqueous phase is raised to 5.4, and the product begins to crystallize out. After 1 hour it is filtered off and dried. The crude yield is 68.8 g.

The product is suspended in water at 25° C., and the pH is lowered to 1.5. After stirring for a short period, the insoluble materials are filtered off, and the filtrate is extracted with ether. The aqueous solution is then cooled to 5° C., and the pH is adjusted to 5.2. The solid which precipitates is filtered off, giving 62.7 g. (58.7% yield) of 6-(D-2-amino-2-phenylacetamido)-2,2-dimethyl-3-(5-tetrazolyl)penam trihydrate, m.p. 201°–202° C., $[\alpha]_D^{25}$ + 228.2 (1% in $CH_3OH$). IR (KBr disc): 1780 $cm^{-1}$ (β-lactam). NMR (in DMSO-$d_6$/$D_2O$): 7.60 ppm (s, 5H), 5.70 ppm (d, 1H), 5.55 ppm (d, 1H), 5.20 ppm (s, 1H), 5115 ppm (d, 1H), 1.50 ppm (s, 3H), 0.09 ppm (s, 3H).

Analysis — Calcd. for $C_{16}H_{19}O_2N_7S \cdot 3H_2O$ (percent): C, 44.95; H, 5.89; N, 22.94; S, 7.50. Found (percent): C, 45.01; H, 5.84; N, 22.81; S, 7.34.

The sodium N-(2-methoxycarbonyl-1-methylvinyl)-D-2-amino-2-phenylacetate is prepared from methyl acetoacetate and D-2-amino-2-phenylacetic acid by the procedure used by Long et al. (J. Chem. Soc., London Part C, 1920 [1971]) for the corresponding p-hydroxy compound.

The MIC of the title compound against a strain of *Streptococcus pyogenes* is <0.1µg/ml.

PREPARATION FF 6-(2-Phenylacetamido)-2,2-dimethyl-3-(1-pivaloyloxymethyl]-tetrazol-5-yl)penam and
6-(2-Phenylacetamido)-2,2-dimethyl-3-(2-[pivaloyloxymethyl]tetrazol-5-yl)penam To a stirred suspension of 10.0 g. (0.0264 mole) of 6-(2-phenylacetamido)-2,2-dimethyl-3-(5-tetrazolyl)penam sodium salt, in 105 ml. of acetone, is added 2.6 ml. of 25% aqueous sodium iodide, followed by 4.35 g. (0.0290 mole) of chloromethyl pivalate. The mixture is refluxed for 4.5 hours, and then it is cooled to ambient temperature. To the mixture is then added 100 ml. of water, and the resulting suspension is extracted with ethyl acetate. The extracts are dried and evaporated to give 6.3 g. of white foam. The MIC of this mixture of the title compounds against *Strep. pyogenes* in 0.2 µg/ml.

The white foam is re-dissolved in a small volume of 80:20 chloroform-ethyl acetate and absorbed on a column of 180 g. of chromatographic grade silica gel. The column is then eluted with 80:20 chloroform-ethyl acetate taking fractions. Each fraction consists of 700 drops of solvent. Fractions 55–95 are combined and evaporated in vacuo to give 2.03 g. of 6-(2-phenylacetamido)-2,2-dimethyl-3-(2-[pivaloyloxymethyl]tetrazol-5-yl)penam. IR (KBr disc): 1785, 1760, 1670 and 1515 $cm^{-1}$. NMR (DMSO-$d_6$/$D_2O$): 7.50 (s, 5H), 6.70 (s, 2H), 6.00–5.60 (m, 2H), 3.85 (s, 2H), 1.65 (s, 3H), 1.36 (s, 9H) and 1.20 (s, 3H) ppm. Fractions 100–164 are combined and evaporated in vacuo to give 0.80 g. of 6-(2-phenylacetamido)-2,2-dimethyl-3-(1-[pivaloyloxymethyl]tetrazol-5-yl)penam. IR (KBr disc): 1780, 1760, 1670 and 1515 $cm^{-1}$. NMR (DMSO-$d_6$($D_2O$): 7.50 (s, 5H) 6.80 (s, 2H), 6.50 (s, 2H), 5.60 (s, 1H), 3.85 (s, 2H), 1.75 (s, 3H), 1.36 (s, 9H) and 1.34 (s, 3H) ppm.

PREPARATION GG 6-(D-2-Amino-2-[p-hydroxyphenyl]acetamido)-2,2-dimethyl-3-(2-[pivaloyloxymethyl]tetrazol-5-yl)penam To a stirred suspension of 287 mg. (1.0 m mole) of sodium N-(2-methoxycarbonyl-1-methylvinyl)-D-2-amino-2-(p-hydroxyphenyl)acetate (Long, et. al., Journal of the Chemical Society [London], Part C, 1920 [1971]) and 1 drop of N-methylmorpholine in 6 ml. of ethyl acetate, is added 0.97 ml. (1.03 mole) of ethylchloroformate, at −15° C. Stirring is continued for a further 30 minutes at −15° C. This mixture is then added to a pre-cooled (−15° C.) suspension of 390.5 mg. (1.0 m mole) of 6-amino-2,2-dimethyl-3-(2-[pivaloyloxymethyl]tetrazol-5-yl)penam hydrochloride in 2 ml. of ethyl acetate containing 101 mg. (1.0 m mole) of triethylamine. The reaction mixture is then stirred at −15° C. for 1 hour followed by 5° C. for 1 hour. The ethyl acetate is removed by evaporation in vacuo, and the white solid thus obtained is suspended in 10 ml. of 1:1 water-tetrahydrofuran. The suspension is cooled to 0° C., and then its pH is adjusted to 2.1. The suspension is stirred at 0° C. for 45 minutes, with further acid being added to maintain the pH at 2.1 as necessary. At this point, the tetrahydrofuran is removed by evaporation in vacuo, the residual aqueous phase is saturated with sodium chloride, and the product is extracted into ethyl acetate. The ethyl acetate is dried and evaporated in vacuo giving, after trituration of the residue with ether, 425 mg. (81% yield) of 6-(D-

2-amino-2-[p-hydroxyphenyl]acetamido)-2,2-dimethyl-3-(2-[pivaloyloxymethyl]tetrazol-5-yl)penam hydrochloride. The infrared spectrum (KBr disc) shows absorptions at 1780 cm$^{-1}$ ($\beta$-lactam) 1755 cm$^{-1}$ (ester), 1682 cm$^{-1}$ (amide I). The NMR spectrum (DMSO-d$_6$) shows absorptions at 7.09 ppm (quartet, 4H, aromatic hydrogens), 6.59 ppm (singlet, 2H, pivaloyloxy methylene), 5.52 ppm (multiplet, 2H, C-5 and C-6 hydrogens), 5.22 ppm (singlet, 1H, side chain methine hydrogen) 5.00 ppm (singlet, 1H, C-3 hydrogen), 1.47 ppm (singlet, 3H, C-2 methyl hydrogen), 1.07 ppm (singlet, 9H, t-butyl hydrogens), and 0.96 ppm (singlet, 3H, C-2 methyl hydrogens).

The MIC of the title compound against Strep. pyogenes is 0.39 $\mu$g./ml.

PREPARATION NH 6-(D-2-Amino-2-[p-hydroxyphenyl]acetamido)-2,2-dimethyl-3-(1-[pivaloyloxymethyl]tetrazol-5-yl)penam The title compound is prepared as its hydrochloride, in 50% yield, from 6-amino-2,2-dimethyl-3-(1-[pivaloyloxymethyl]tetrazol-5-yl)penam, using the procedure of Preparation GG. IR (KBr disc): 1780 cm$^{-1}$ ($\beta$-lactam) and 1680 cm$^{-1}$ (amide I). NMR (DMSO-d$_6$): 7.09 ppm (quartet, 4H), 6.55 ppm (singlet, 2H), 5.61 ppm (multiplet, 3H), 5.06 ppm (singlet, 1H), 1.55 ppm (singlet, 3H), 1.10 ppm (singlet, 3H), 1.10 ppm (singlet, 9H) and 1.03 ppm (singlet, 3H).

PREPARATION II

6-Phenylacetamido)-2,2-dimethyl-3-(1-[2]-[1-acetoxyethyl]tetrazol-5-yl)penam

Reaction of 6-(2-phenylacetamido)-2,2-dimethyl-3-(5-tetrazolyl)penam sodium salt with 1-acetoxyethyl chloride, according to the procedure of Preparation FF produces the title compound as a mixture of isomers, m.p. 55°–70° C., yield 28%. IR (KBr disc): 1780, 1770, 1670 and 1515 cm$^{-1}$. NMR (CDCl$_3$): 7.20 (s, 6H), 6.25 (m, 1H), 5.75–5.40 (m, 2H), 5.20 (s, 1H), 3.60 (s, 2H), 2.00 (m, 6H), 1.45 (s, 3H) and 0.95 (s, 3H) ppm.

PREPARATION JJ 6-(2-Phenylacetamido)-2,2-dimethyl-3-(1-[2]-[3-phthalidyl]

Reaction of 6-(2-phenylacetamido)-2,2-dimethyl-3-(5-tetrazolyl)penam sodium salt with 3-bromophthalide, according to the procedure of Preparation GG produces the title compound as a mixture of isomers, m.p. 70°–85° C., yield 91%. IR (KBr disc): 1785, 1675 and 1500 cm$^{-1}$. NMR (CDCl$_3$): 8.05–7.10 (m, 9H), 6.55–6.20 (m, 2H), 5.80 (m, 2H), 5.20 (m, 1H), 3.60 (s, 2H), 1.60 (s, 3H) and 1.00 (s, 3H) ppm.

What is claimed is:
1. A compound of the formula

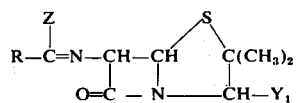

wherein R is selected from the group consisting of benzyl and phenoxymethyl; wherein Y$_1$ is selected from the group consisting of

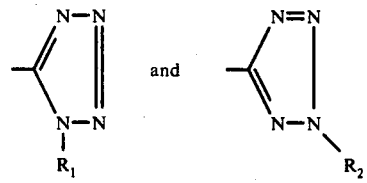

wherein R$_1$ is selected from the group consisting of R$_2$ and a tetrazolylpenam nitrogen protecting group; R$_2$ is selected from the group consisting of hydrogen, trialkylsilyl having from one to four carbon atoms per alkyl group, alkanoyloxymethyl having from three to eight carbon atoms, 1-alkanoyloxyethyl having from four to nine carbon atoms, phthalidyl and

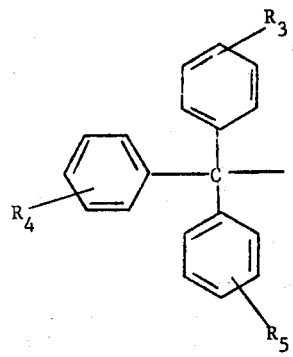

wherein R$_3$, R$_4$, and R$_5$ are each selected from the group consisting of hydrogen, chloro, bromo, fluoro, alkyl having from one to four carbon atoms, alkoxy having from one to four carbon atoms and phenyl, and Z is selected from the group consisting of chloro and OR' wherein R' is selected from the group consisting of alkyl of 1 to 4 carbon atoms, phenylalkyl of 1 to 3 alkyl carbon atoms, hydroxyalkyl of 2 to 4 carbon atoms, alkoxyalkyl of 3 to 6 carbon atoms, 2-(p-methoxy-benzyloxy)ethyl, and hydroxy-alkoxyalkyl of 4 to 7 carbon atoms; with the proviso that when Z is chloro, R$_1$ and R$_2$ are other than hydrogen.

2. A compound according to claim 1 wherein Z is OR'.

3. A compound according to claim 1 wherein Z is chloro.

4. A compound according to claim 3 wherein R is benzyl.

5. A compound according to claim 3 wherein R is phenoxymethyl.

* * * * *

UNITED STATES PATENT AND TRADEMARK OFFICE
CERTIFICATE OF CORRECTION

PATENT NO. : 3,994,939
DATED : NOVEMBER 30, 1976
INVENTOR(S) : RONNIE D. CARROLL, East Lyme, Conn.

It is certified that error appears in the above-identified patent and that said Letters Patent are hereby corrected as shown below:

Col. 9, line 47, "3° C." should read -- 30° C. -- ;

Col. 16, line 36, "methylbenzyl" should read -- methoxybenzyl -- ;

Col. 28, line 42, "(4.3.9)" should read -- (4.3.0) -- ;

Col. 31, line 60, "bis-triisopropyl" should read -- bis-triisopropylsilyl --;

Col. 33, line 56, "0.09 ppm" should read -- 0.90 ppm -- ;

Col. 35, line 31, "6-Phenylacetamido)" should read -- 6-(2-Phenylacetamido) -- ; line 45, "phthalidyl]" should read -- phthalidyl]tetrazol-5-yl)penam -- .

Signed and Sealed this

Seventeenth Day of May 1977

[SEAL]

Attest:

RUTH C. MASON
Attesting Officer

C. MARSHALL DANN
Commissioner of Patents and Trademarks